(12) United States Patent
Kleppen et al.

(10) Patent No.: US 10,883,074 B2
(45) Date of Patent: Jan. 5, 2021

(54) BIOREACTOR AND USES THEREOF

(71) Applicant: ACD Pharmaceuticals AS, Leknes (NO)

(72) Inventors: Hans Petter Kleppen, Oslo (NO); Eirik Bardsen, Oslo (NO); Juan Jose Jimenez Martinez, As (NO)

(73) Assignee: ACD Pharmaceuticals AS

( * ) Notice: Subject to any disclaimer, the term of this patent is extended or adjusted under 35 U.S.C. 154(b) by 396 days.

(21) Appl. No.: 15/315,824

(22) PCT Filed: Jun. 2, 2015

(86) PCT No.: PCT/GB2015/051613
§ 371 (c)(1),
(2) Date: Dec. 2, 2016

(87) PCT Pub. No.: WO2015/185923
PCT Pub. Date: Dec. 10, 2015

(65) Prior Publication Data
US 2017/0101612 A1    Apr. 13, 2017

Related U.S. Application Data

(60) Provisional application No. 62/007,075, filed on Jun. 3, 2014.

(51) Int. Cl.
| *C12M 1/107* | (2006.01) |
| *C12M 1/00* | (2006.01) |
| *C12M 1/21* | (2006.01) |
| *C12M 3/00* | (2006.01) |
| *C12M 1/02* | (2006.01) |
| *C12M 1/12* | (2006.01) |

(52) U.S. Cl.
CPC ............ *C12M 21/04* (2013.01); *C12M 21/08* (2013.01); *C12M 21/14* (2013.01); *C12M 23/02* (2013.01); *C12M 23/06* (2013.01); *C12M 23/34* (2013.01); *C12M 27/00* (2013.01); *C12M 29/08* (2013.01); *C12M 29/20* (2013.01); *C12M 41/02* (2013.01)

(58) Field of Classification Search
CPC ...... C12M 21/04; C12M 21/08; C12M 21/14; C12M 23/02; C12M 23/06; C12M 23/34; C12M 27/00; C12M 29/08; C12M 29/20; C12M 41/02
See application file for complete search history.

(56) References Cited

U.S. PATENT DOCUMENTS

| 4,340,484 A * | 7/1982 | Pollock | C02F 1/24 |
| | | | 210/607 |
| 4,380,584 A | 4/1983 | Hitzman | |
| 4,808,419 A | 2/1989 | Hsu | |
| 2011/0207218 A1* | 8/2011 | Staheli | B01F 3/04241 |
| | | | 435/394 |
| 2013/0082410 A1* | 4/2013 | Goodwin | B01F 15/0085 |
| | | | 261/42 |

FOREIGN PATENT DOCUMENTS

| CA | 1 114 960 | 12/1981 |
| DE | 255 4118 | 6/1976 |
| DE | 293 6092 | 4/1980 |
| DE | 414 2967 | 7/1993 |
| DE | 697 021 87 | 12/2000 |

OTHER PUBLICATIONS

EU Patent Office, PCT International Search Report, PCT/GB2015/051613, dated Sep. 21, 2015.

* cited by examiner

*Primary Examiner* — Blaine Lankford
(74) *Attorney, Agent, or Firm* — Emerson Thomson Bennett, LLC; Daniel A. Thomson

(57) ABSTRACT

The present invention relates to the field of fermentation. In particular, the present invention relates to a method and apparatus for production of products by use of living cells or active components derived from such cells using a bioreactor having a built in gas distributor and a specific system/device for handling foam formed in the process. The invention also relates to a bioreactor comprising: a reaction chamber having a fermentation zone and a foam settling zone, wherein the reaction chamber is arranged such that the foam settling zone is spaced from or physically separated from the fermentation zone so as to reduce the effect of activity in the fermentation zone on foam in the settling zone. The separation of the fermentation zone from the activity of the fermentation zone encourages settling of the foam. The invention also provides a method of forming a bioreactor comprising: overlapping two flat, flexible sheets of material; and causing said two sheets to adhere to each other in selected areas so as to define a reaction chamber. This is a particularly cost-effective way to produce a single use, disposable reactor.

14 Claims, 8 Drawing Sheets

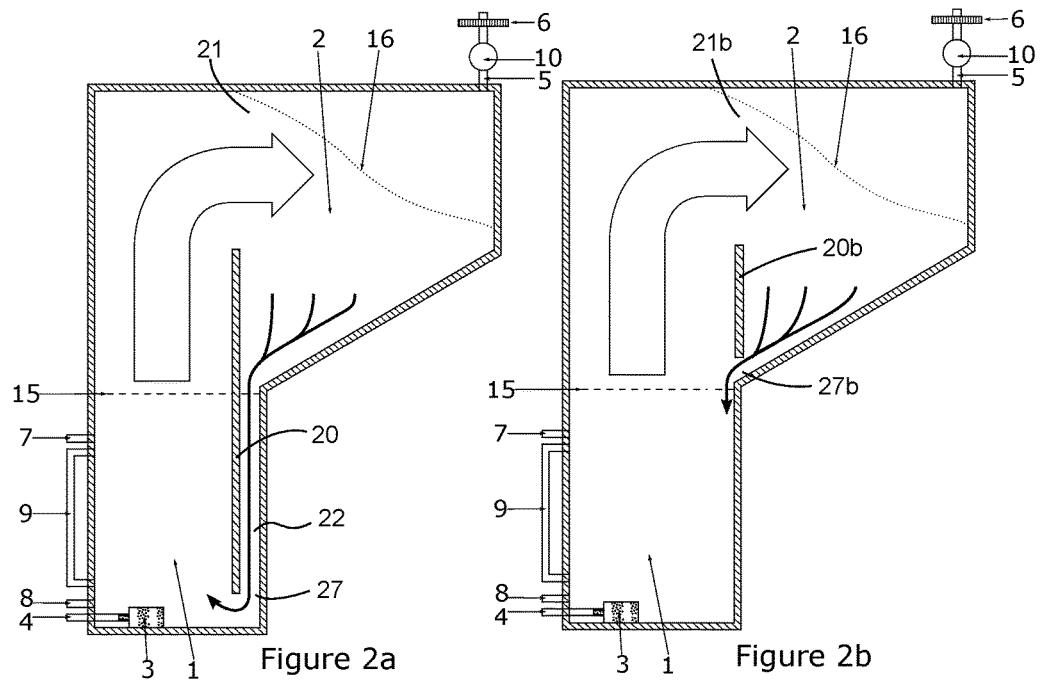
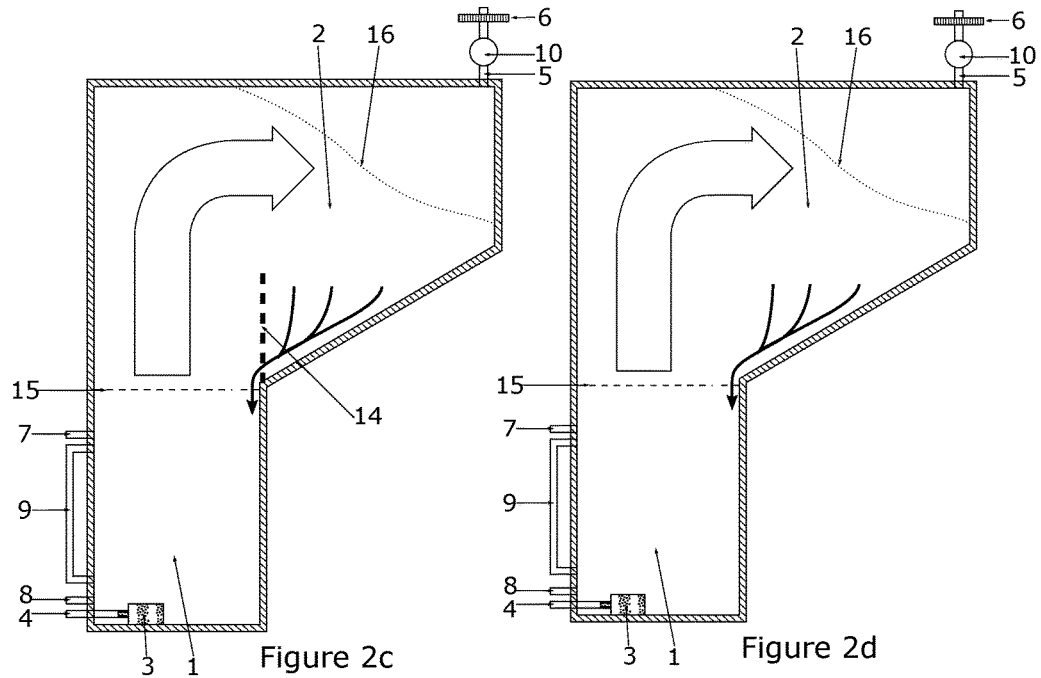

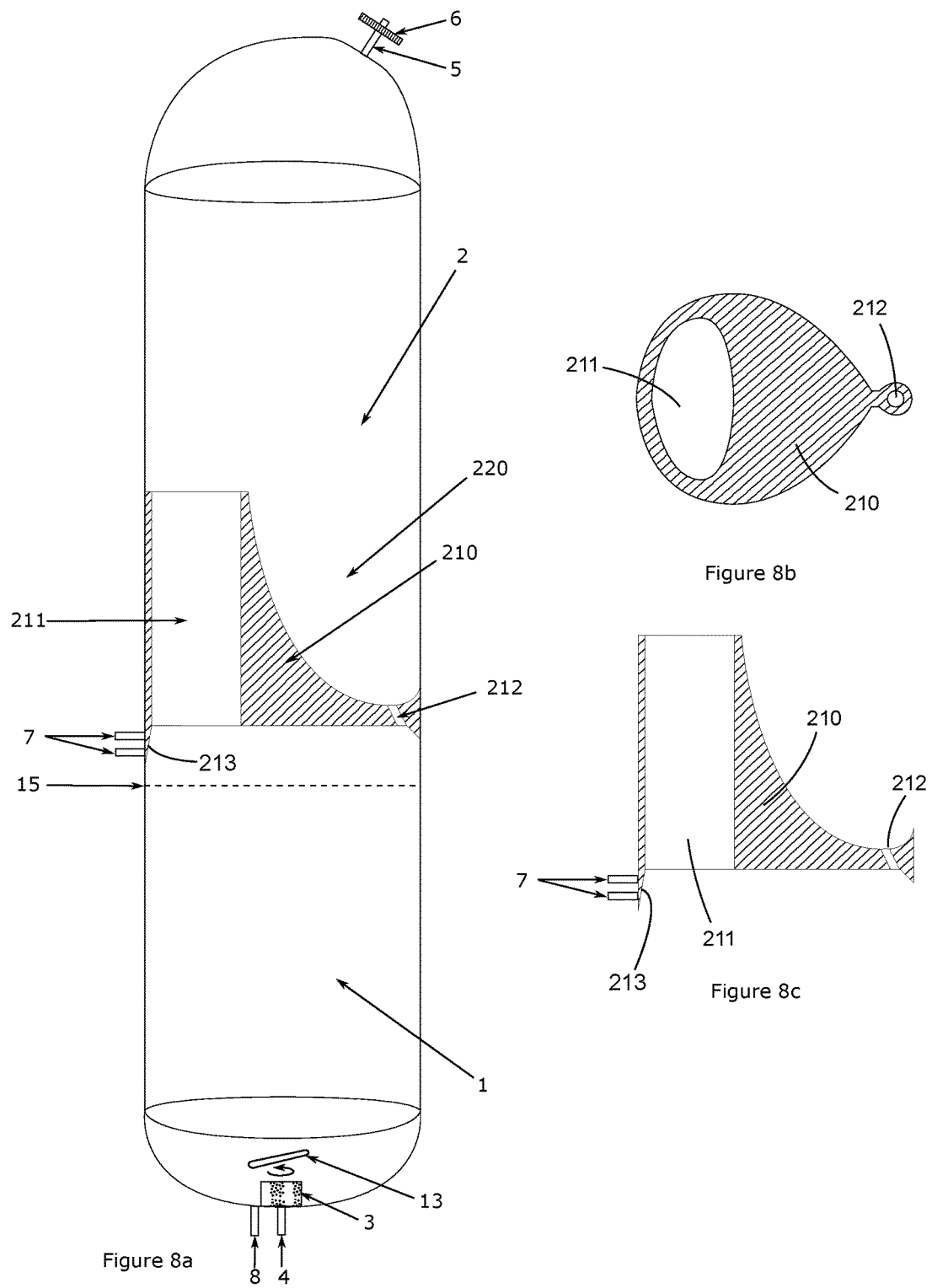

BIOREACTOR AND USES THEREOF

FIELD OF THE INVENTION

The present invention relates to the field of fermentation. In particular, the present invention relates to a method and apparatus for production of products by use of living cells or active components derived from such cells using a bioreactor having a built in gas distributor and a specific system/device for handling foam formed in the process.

BACKGROUND OF THE INVENTION

Several commercial products are prepared in a bioreactor or fermenter (hereafter common term bioreactor) by use of living cells, living organisms or active components derived from such cells or organisms. Typical such components are biocatalysts including enzymes and cellular organelles.

The cells include any living cells useful for the biochemical process and include animal cells, human cells, insect cells, plant cells, fungal cells, molds, algal cells, protozoa, archaea, and bacteria. Living organisms can be any living organism useful for production of products and include for example algae, fungi, nematodes, and plants.

These commercial products include various chemicals, food, food components, food additives, feed, feed components, feed additives, beverages, beverages components, beverages additives, prebiotics, probiotics, biocides, pharmaceuticals, industrial enzymes, and other products like industrial chemicals, chemicals in household products, food and beverages.

The pharmaceutical production includes drugs like various biological drugs which are protein-based drugs, steroids and antibiotics. Other pharmaceutical products include immunologicals, for example whole cell vaccines or vaccines based on purified cell components, like proteins, carbohydrates, lipids, DNA or RNA, or combinations of such components.

There is today an increasing interest in protein derived drugs like for example insulins, growth hormones, enzymes, interleukins, monoclonal antibodies, bacteriocins, and bioactive peptides. There is also an increasing interest in therapeutic use of viruses, for example in gene therapy and bacteriophage therapy.

There is also increasing interest in single use bioreactors due to lower cost, reduced risk of cross contamination and lower risk of bacteriophage infections interfering with the fermentation.

Additional bioreactors are needed to improve efficiency of biological reactions.

SUMMARY OF THE INVENTION

The present invention relates to the field of fermentation. In some preferred aspects, the present invention relates to a method and apparatus for production of products by use of living cells or active components derived from such cells using a bioreactor having a built in gas distributor and a specific system/device for handling foam formed in the process.

For example, in some embodiments, the present disclosure provides a bioreactor, comprising: at least one fermentation compartment and at least one foam compartment where foam is transported back to the fermentation mixture in the form of liquid, wherein the fermentation and foam compartments are separated by a wall that is absent or permeable for foam in the upper part of the reactor and is absent or permeable for liquid in a lower part of the reactor. In some embodiments, the bioreactor comprises at least two fermentation compartments and/or at least two foam compartments. In some embodiments, the bioreactor further comprises a gas sparger. In some embodiments, the gas sparger comprises a gas inlet and/or a stirring device or agitation device (e.g., magnetic propeller). In some embodiments, the bioreactor further comprises a gas outlet, gas outlet filter and a pressure control. In some embodiments, the gas outlet and said pressure control are on the same assembly or in physically different locations of said bioreactor. In some embodiments, the bioreactor comprises a foam transfer component configured to transfer foam from the fermentation compartment to the foam compartment. In some embodiments, the bioreactor further comprises a culture transfer component configured to recycle cultures to the fermentation compartment. In some embodiments, the bioreactor comprises at least one waste compartment in addition to at least one fermentation compartment and at least one foam compartment. In some embodiments, the bioreactor further comprises at least one component selected from a filling inlet, a filling outlet, or a monitor loop. In some embodiments, the bioreactor is disposable. In some embodiments, the foam transport component transports foam based on gravity. In some embodiments, the bioreactor is a gas-lift reactor.

Further embodiments provide the use or a method of using any of the aforementioned bioreactors in the fermentation of a living organism or active component thereof. In some embodiments, the organism is selected from, for example, a bacterium, a virus (e.g., bacteriophage), an animal cell (e.g., human cell), an insect cell, a plant cell, a fungus, an algal cell, a protist cell, an archae cell, or an active component of any of the aforementioned cells or viruses. In some embodiments, the fermentation is anaerobic or aerobic. In some embodiments, the fermentation produces a drug, active pharmaceutical agent, or drug precursor (e.g., a protein (e.g., antibody), a protein derivative, a small molecule, or a living non-human organism). In some embodiments, the fermentation product is for use in a pharmaceutical product. In some embodiments, the drug, active pharmaceutical agent, living non-human organism or drug precursor is for use in the treatment of cancer, infections, or immunological disease. In some embodiments, the loss of fermentation product is reduced by at least one half relative to the loss in a one-compartment reactor.

According to one aspect, the invention provides a bioreactor comprising: a reaction chamber having a fermentation zone and a foam settling zone, wherein the reaction chamber is arranged such that the foam settling zone is spaced from or physically separated from the fermentation zone so as to reduce the effect of activity in the fermentation zone on foam in the settling zone.

In a traditional reactor, the single reactor chamber simply accumulates foam directly above the fermentation zone. Gas is typically vented from the top of the reaction chamber via a gas outlet and filter. The reactor must be designed with sufficient height that the foam generated during operation does not reach the gas outlet and filter. If it does so, the filter can become clogged and/or wetted, thus becoming inoperational. This leads to a pressure increase which may ruin the batch, or even rupture the reactor.

The quantity of foam produced during a process can vary depending on a number of factors such as the particular culture or fermentation mixture being used (e.g. its viscosity affects foam formation), gas sparging and the mixing equipment and/or mixing speed. Thus foam formation can be difficult to predict and the quantity can vary significantly between batches.

By providing a settling zone spaced from or physically separated from the fermentation zone, the foam will be separated from the activity of the fermentation zone, and can settle, i.e. deflate and lose its volume, returning to liquid. The activity in the fermentation zone may arise from the fermentation process itself and/or from mixing and/or gas sparging.

The term "spaced from" is intended to cover adjacent zones of the same reactor as well as different chambers partially separated from one another by some form of barrier or boundary.

The foam settling zone may be formed as a laterally enlarged section of the reaction chamber. By forming the settling zone as a laterally enlarged section, the height of the reaction chamber can be minimised. The enlarged volume provides room to accommodate more foam without increasing the height, while the lateral spacing removes the foam from the active part of the reaction chamber, thus permitting settling and re-liquefying to take place. The enlarged section could be formed as an enlarged annulus around a cylindrical main chamber. However, in some preferred embodiments the foam settling zone is positioned to one side of the fermentation zone. This is particularly advantageous for certain manufacturing techniques discussed further below. For example, a reaction chamber formed from flat, flexible sheets can advantageously be formed with a settling zone to one or both sides of the fermentation zone. When the bioreactor is in use, the foam settling zone is preferably located above the level of the fermentation mixture or culture medium (i.e. above the maximum liquid level) and off to one side so that there is no interference between the turbulent fluid/rising bubbles and the settling foam. The larger volume also accommodates an increased foam level that might occur due to process variations and thus the reactor can be more robust to process variations.

Preferably the foam settling zone has a bottom wall that slopes downwardly towards the fermentation zone so that settled foam (i.e. liquefied fermentation mixture) can flow to the fermentation zone under gravity.

The fermentation zone and the settling zone may be formed as different regions in the same reaction chamber, but in full communication with one another. Alternatively, in some embodiments a barrier may be disposed so as to partially separate the fermentation zone from the foam settling zone. The barrier serves to further isolate the settling foam from the activity in the fermentation chamber (i.e. in and above the fermentation mixture), i.e. it can provide greater physical separation and reduced interaction between the zones. The position of the barrier can be varied significantly so long as it achieves the goal of separation. For example it may be a vertical barrier, substantially parallel with a wall of the fermentation zone or it may be angled so as to enlarge the settling zone in the upper part thereof.

The barrier may be made from a variety of materials, but is preferably substantially impermeable to liquid and foam. As described below, a reactor is may be formed by welding two flexible sheets together. The barrier may then be formed by one or more additional welds between the sheets.

The barrier must allow settled foam to drain back as liquid into the fermentation zone and thus should not close off the lower part of the settling zone. The barrier must also allow foam to enter the settling zone and thus should not fully close off or excessively restrict the fermentation zone. Preferably the barrier forms a large aperture for passage of foam from the fermentation zone to the foam settling zone and a small aperture for passage of settled foam (i.e. liquefied fermentation mixture) as liquid from the foam settling zone to the fermentation zone. The terms "large" and "small" here are relative to each other. Additionally, the term "small" means small in relation to the size of the foam structure. If the return passage to the fermentation zone feeds back above the normal level of fermentation mixture, then it is open to newly formed foam and should thus be small enough to prevent foam from rising up through said return passage into the foam settling zone. A sufficiently small aperture will not permit this, particularly when the weight of returning liquid blocks the lighter foam. The structure of the foam (and thus the size of the aperture for passage of foam) will depend on a number of factors such as the particular culture medium/fermentation mixture being used (e.g. its viscosity) and the degree of mixing/agitation taking place. Different sizes of apertures may be used for reactors of different intended uses.

In some embodiments the barrier may extend along one side of the fermentation zone so as to form a passage between the barrier and the reaction chamber for transfer of settled culture medium from the foam settling zone to the fermentation zone. This structure is particularly simple to form and thus facilitates cost-effective manufacture which is especially important in the case of single use, disposable reactors.

The return aperture can feed back to an upper part of the fermentation zone, e.g. above the normal, expected level of fermentation mixture/culture medium. However, preferably it connects to a lower part of the fermentation zone. This is effective in avoiding newly formed foam from entering the settling zone through the return aperture as new foam is formed above the level of the connection between the two zones. In this case, the size of the aperture is not so restricted.

In some preferred embodiments, the return aperture is arranged to drain liquid onto a wall of the reaction chamber so as to provide a smoother return flow (e.g. avoiding dripping and/or splashing).

In some preferred embodiments, the reactor further comprises a separator that separates the fermentation zone from the foam settling zone and the separator comprises a large aperture for passage of foam from the fermentation zone to the foam settling zone and a small aperture for passage of settled foam from the foam settling zone to the fermentation zone. Such a separator may be used in embodiments in which the settling zone is not displaced laterally from the fermentation zone. Instead, the settling zone may be positioned above the fermentation zone, but is separated therefrom by the separator, thus preventing the activity of the fermentation zone from negatively impacting the settling process. This construction is particularly advantageous when the separator is formed as an insert that can be bonded (e.g. welded) to one or more other chamber parts.

In some preferred embodiments the foam settling zone is formed as a separate compartment from the fermentation zone. The zones are thus formed as completely separate chambers, interconnected via at least two conduits, one for foam transfer into the settling chamber and one for return of liquid to the fermentation chamber. Preferably the return conduit is formed with a downward slope so that the liquid can flow under gravity, without the need for a pump.

A gas outlet is preferably provided in an upper region of the foam settling zone. The gas outlet may be located to one side of the foam settling zone laterally away from the fermentation zone. Forming the gas outlet far from the foam formation zone reduces the chances of the gas outlet and any associate filter from clogging in the event of excessive or unanticipated foam formation.

The bioreactor may further comprise a waste chamber fluidly connected to an upper portion of the foam settling zone and further comprising a gas outlet located in the waste chamber instead of in the foam settling zone. The waste chamber provides an overflow area which is able to accommodate situations in which excess foam is produced without risking clogging of the gas outlet and/or filter. Normal amounts of foam can be settled and returned to the fermentation zone as described above. However, as the outlet is located in the waste chamber, it will not be at risk of being affected by foam until an overflow situation has arisen. As no gas outlet and no filter are provided in the foam settling zone, there is no risk of clogging or filter wetting even if the foam settling zone completely fills with foam. The waste chamber may not have any return mechanism for settled foam and thus any foam which does overflow into the waste chamber will result in a loss of fermentation mixture. However, generally, the reactor is designed so that overflow into the waste chamber will only happen in unusual or short-lived conditions and thus wastage will be small. Such wastage is acceptable given the advantage of avoiding an outlet clogging situation which could ruin the whole batch.

In preferred embodiments, the gas outlet may be positioned at an upper portion of the waste chamber and the fluid connection from the foam settling zone may connect at a lower portion of the waste chamber. The gas outlet and the connection from the foam settling zone may be located on opposite sides of the waste chamber. These designs help to maximise the separation of the gas outlet from any excess foam that enters the waste chamber, thus minimising the risk of a filter clogging condition.

The waste chamber may be located underneath the foam settling zone and adjacent the fermentation zone. This is an efficient design, making use of otherwise wasted space. The waste chamber advantageously makes use of space that cannot be used for the foam settling zone. For example, in many designs the foam settling zone will be located higher than a normal liquid level of the fermentation zone so that settled foam can flow back under gravity. The area under the settling zone is not otherwise used and so can be used for a waste chamber that adds robustness to the reactor in relation to excess foam formation.

The bioreactor may be formed in many ways and from different materials. For example the bioreactor may be formed from steel, but is preferably formed from plastic which is less costly and more suitable for disposable reactors. In some particularly preferred embodiments the bioreactor is formed from two flexible sheets overlapped with each other and welded together to form the reaction chamber and any additional internal structure. In this way, very cost-effective reactors can be manufactured quickly and inexpensively such that they can be considered single-use and disposable. Welds between the two sheets can be used to form an overall perimeter around the reaction chamber as well as forming any additional barriers and/or connecting passages that are required and a waste chamber if required. This technique is also applicable to bioreactors in which a foam settling chamber is formed separately from a fermentation chamber. The two chambers may be formed in the same two overlapped sheets, with connecting conduits also formed from the two overlapped sheets by additional welds. Alternatively two separate chambers may be formed with additional separate conduits added later.

Preferably the bioreactor comprises a mixing device at a lower portion of the fermentation zone. The mixing device is used to improve the reaction efficiency in the fermentation zone and is often partly responsible for (or increases) the formation of foam. The mixing device may comprise an agitator such as a magnetic stirrer. The mixing device may comprise a gas sparger that releases gas bubbles into the mixture that rise, causing agitation and mixing as well as possibly being an important part of the reaction.

According to another aspect, the invention provides a method of forming a bioreactor comprising: overlapping two flat, flexible sheets of material; and causing said two sheets to adhere to each other in selected areas so as to define a reaction chamber. The selected areas may further define a barrier inside said reaction chamber that partially separates the reaction chamber into two zones. The selected areas may further define a conduit that connects one or more regions of the bioreactor together.

It will be appreciated that the adhering may be by any suitable means such as using adhesives or other bonding methods, but in some preferred methods involves welding the two sheets together in the selected areas. It will also be appreciated that this method may be used to form any of the walls, barriers, conduits, passages, chambers and/or zones discussed above.

One aspect of the present invention relates to a bioreactor for fermentation characterized by comprising of at least two compartments where the compartments are separated by a wall that is absent or permeable for foam in the upper part of the reactor and is absent or permeable for liquid in a lower part of the reactor, and where at least one compartment is the compartment where the fermentation takes place and at least one compartment is where foam is transported back to the fermentation mixture in the form of liquid.

A more preferred aspect of the present invention relates to a bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid.

A more preferred aspect of the present invention relates to a bioreactor for fermentation characterized by comprising of three compartments where one compartment is the fermentation compartment, one compartment is the foam handling compartment where foam is transported back to the fermentation mixture in the form of liquid and one compartment is the waste compartment, and where the fermentation compartment and the foam handling compartment is separated by a wall that is absent or permeable for foam in the upper part of the reactor and absent or permeable for liquid in a lower part of the reactor, and where the foam handling compartment and the waste compartment is separated by a wall that is absent or permeable for foam in the upper part of the reactor.

A more preferred aspect of the present invention relates to a bioreactor for fermentation characterized by comprising of at least three compartments where at least one compartment is the fermentation compartment, at least one compartment is the foam handling compartment where foam is transported back to the fermentation mixture in the form of liquid and at least one compartment is the waste compartment, and where the fermentation compartments and the foam handling compartments are separated by walls which are absent or permeable to foam in the upper part of the reactor and absent or permeable to liquid in a lower part of the reactor, and where foam handling compartments and waste compartments are separated by walls which are absent or permeable for foam in the upper part of the reactor.

A more preferred aspect of the present invention relates to a bioreactor for fermentation characterized by comprising of at least two compartments where the compartments are separated by a wall that is absent or permeable for foam in the upper part of the reactor and is absent or permeable for liquid in a lower part of the reactor, and where at least one compartment is the compartment where the fermentation takes place and at least one compartment is where foam is transported back to the fermentation mixture in the form of liquid based on gravitation.

A more preferred aspect of the present invention relates to a bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation.

A more preferred aspect of the present invention relates to a bioreactor for fermentation characterized by comprising of three compartments where one compartment is the fermentation compartment, one compartment is the foam handling compartment where foam is transported back to the fermentation mixture in the form of liquid based on gravitation and one compartment is the waste compartment, and where the fermentation compartment and the foam handling compartment is separated by a wall that is absent or permeable for foam in the upper part of the reactor and absent or permeable for liquid in a lower part of the reactor, and where the foam handling compartment and the waste compartment is separated by a wall that is absent or permeable for foam in the upper part of the reactor.

A more preferred aspect of the present invention relates to a bioreactor for fermentation characterized by comprising of at least three compartments where at least one compartment is the fermentation compartment, at least one compartment is the foam handling compartment where foam is transported back to the fermentation mixture in the form of liquid based on gravitation and at least one compartment is the waste compartment, and where the fermentation compartments and the foam handling compartments are separated by walls which are absent or permeable to foam in the upper part of the reactor and absent or permeable to liquid in a lower part of the reactor, and where foam handling compartments and waste compartments are separated by walls which are absent or permeable for foam in the upper part of the reactor.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid.

A more preferred aspect of the present invention relates to a disposable bioreactor for fermentation characterized by comprising of at least two compartments where the compartments are separated by a wall that is absent or permeable for foam in the upper part of the reactor and is absent or permeable for liquid in a lower part of the reactor, and where at least one compartment is the compartment where the fermentation takes place and at least one compartment is where foam is transported back to the fermentation mixture in the form of liquid based on gravitation.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation.

A more preferred aspect of the present invention relates to a disposable bioreactor for fermentation characterized by comprising of three compartments where one compartment is the fermentation compartment, one compartment is the foam handling compartment where foam is transported back to the fermentation mixture in the form of liquid based on gravitation and one compartment is the waste compartment, and where the fermentation compartment and the foam handling compartment is separated by a wall that is absent or permeable for foam in the upper part of the reactor and absent or permeable for liquid in a lower part of the reactor, and where the foam handling compartment and the waste compartment is separated by a wall that is absent or permeable for foam in the upper part of the reactor.

A more preferred aspect of the present invention relates to a disposable bioreactor for fermentation characterized by comprising of at least three compartments where at least one compartment is the fermentation compartment, at least one compartment is the foam handling compartment where foam is transported back to the fermentation mixture in the form of liquid based on gravitation and at least one compartment is the waste compartment, and where the fermentation compartments and the foam handling compartments are separated by walls which are absent or permeable to foam in the upper part of the reactor and absent or permeable to liquid in a lower part of the reactor, and where foam handling compartments and waste compartments are separated by walls which are absent or permeable for foam in the upper part of the reactor.

Another preferred aspect of the present invention relates to a multi-use bioreactor for fermentation characterized by comprising of at least two compartments where the compartments are separated by a wall that is absent or permeable for foam in the upper part of the reactor and is absent or permeable for liquid in a lower part of the reactor, and where at least one compartment is the compartment where the fermentation takes place and at least one compartment is where foam is transported back to the fermentation mixture in the form of liquid.

A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation.

A more preferred aspect of the present invention relates to a multi-use bioreactor for fermentation characterized by comprising of at least two compartments where the compartments are separated by a wall that is absent or permeable for foam in the upper part of the reactor and is absent or permeable for liquid in the lower part of the reactor, and where at least one compartment is the compartment where the fermentation takes place and at least one compartment is where foam is transported back to the fermentation mixture in the form of liquid based on gravitation.

A more preferred aspect of the present invention relates to a multi-use bioreactor for fermentation characterized by comprising of three compartments where one compartment is the fermentation compartment, one compartment is the foam handling compartment where foam is transported back to the fermentation mixture in the form of liquid based on gravitation and one compartment is the waste compartment, and where the fermentation compartment and the foam handling compartment is separated by a wall that is absent or permeable for foam in the upper part of the reactor and absent or permeable for liquid in a lower part of the reactor, and where the foam handling compartment and the waste compartment is separated by a wall that is absent or permeable for foam in the upper part of the reactor.

A more preferred aspect of the present invention relates to a multi-use bioreactor for fermentation characterized by comprising of at least three compartments where at least one compartment is the fermentation compartment, at least one compartment is the foam handling compartment where foam is transported back to the fermentation mixture in the form of liquid based on gravitation and at least one compartment is the waste compartment, and where the fermentation compartments and the foam handling compartments are separated by walls which are absent or permeable to foam in the upper part of the reactor and absent or permeable to liquid in a lower part of the reactor, and where foam handling compartments and waste compartments are separated by walls which are absent or permeable for foam in the upper part of the reactor.

A more preferred aspect of the present invention relates to a disposable bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on bacterial cells or active components derived from bacterial cells.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on bacterial cells or active components derived from bacterial cells.

A more preferred aspect of the present invention relates to a disposable bioreactor for fermentation characterized by comprising of three compartments where one compartment is the fermentation compartment, one compartment is the foam handling compartment where foam is transported back to the fermentation mixture in the form of liquid and one compartment is the waste compartment, and where the fermentation compartment and the foam handling compartment is separated by a wall that is absent or permeable for foam in the upper part of the reactor and absent or permeable for liquid in a lower part of the reactor, and where the foam handling compartment and the waste compartment is separated by a wall that is absent or permeable for foam in the upper part of the reactor, and where the fermentation is based on bacterial cells or active components derived from bacterial cells.

A more preferred aspect of the present invention relates to a disposable bioreactor for fermentation characterized by comprising of at least three compartments where at least one compartment is the fermentation compartment, at least one compartment is the foam handling compartment where foam is transported back to the fermentation mixture in the form of liquid and at least one compartment is the waste compartment, and where the fermentation compartments and the foam handling compartments are separated by walls which are absent or permeable to foam in the upper part of the reactor and absent or permeable to liquid in a lower part of the reactor, and where foam handling compartments and waste compartments are separated by walls which are absent or permeable for foam in the upper part of the reactor, and where the fermentation is based on bacterial cells or active components derived from bacterial cells.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation and where the fermentation is based on bacteria cells or active components derived from bacteria cells.

A more preferred aspect of the present invention relates to a disposable bioreactor for fermentation characterized by comprising of three compartments where one compartment is the fermentation compartment, one compartment is the foam handling compartment where foam is transported back to the fermentation mixture in the form of liquid based on gravitation and one compartment is the waste compartment, and where the fermentation compartment and the foam handling compartment is separated by a wall that is absent or permeable for foam in the upper part of the reactor and absent or permeable for liquid in a lower part of the reactor, and where the foam handling compartment and the waste compartment is separated by a wall that is absent or permeable for foam in the upper part of the reactor, and where the fermentation is based on bacterial cells or active components derived from bacterial cells.

A more preferred aspect of the present invention relates to a disposable bioreactor for fermentation characterized by comprising of at least three compartments where at least one compartment is the fermentation compartment, at least one compartment is the foam handling compartment where foam is transported back to the fermentation mixture in the form of liquid based on gravitation and at least one compartment is the waste compartment, and where the fermentation compartments and the foam handling compartments are separated by walls which are absent or permeable to foam in the upper part of the reactor and absent or permeable to liquid in a lower part of the reactor, and where foam handling compartments and waste compartments are separated by walls which are absent or permeable for foam in the upper part of the reactor, and where the fermentation is based on bacterial cells or active components derived from bacterial cells.

A more preferred aspect of the present invention relates to a multi-use bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on bacterial cells or active components derived from bacterial cells.

A more preferred aspect of the present invention relates to a multi-use bioreactor for fermentation characterized by comprising of three compartments where one compartment is the fermentation compartment, one compartment is the foam handling compartment where foam is transported back to the fermentation mixture in the form of liquid based on gravitation and one compartment is the waste compartment, and where the fermentation compartment and the foam handling compartment is separated by a wall that is absent or permeable for foam in the upper part of the reactor and absent or permeable for liquid in a lower part of the reactor, and where the foam handling compartment and the waste compartment is separated by a wall that is absent or permeable for foam in the upper part of the reactor, and where the fermentation is based on bacterial cells or active components derived from bacterial cells.

A more preferred aspect of the present invention relates to a multi-use bioreactor for fermentation characterized by comprising of at least three compartments where at least one compartment is the fermentation compartment, at least one compartment is the foam handling compartment where foam is transported back to the fermentation mixture in the form of liquid based on gravitation and at least one compartment is the waste compartment, and where the fermentation compartments and the foam handling compartments are separated by walls which are absent or permeable to foam in the upper part of the reactor and absent or permeable to liquid in a lower part of the reactor, and where foam handling compartments and waste compartments are separated by walls which are absent or permeable for foam in the upper part of the reactor, and where the fermentation is based on bacterial cells or active components derived from bacterial cells.

A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on bacterial cells or active components derived from bacterial cells.

A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation and where the fermentation is based on bacterial cells or active components derived from bacterial cells.

A more preferred aspect of the present invention relates to a disposable bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based fungal cells or active components derived from fungal cells.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on fungal cells or active components derived from fungal cells.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation and where the fermentation is based on fungal cells or active components derived from fungal cells.

A more preferred aspect of the present invention relates to a multi-use bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based fungal cells or active components derived from fungal cells A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on fungal cells or active components derived from fungal cells A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation and where the fermentation is based on fungal cells or active components derived from fungal cells A more preferred aspect of the present invention relates to a disposable bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on animal cells or active components derived from animal cells.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on animal cells or active components derived from animal cells.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation and where the fermentation is based on animal cells or active components derived from animal cells.

A more preferred aspect of the present invention relates to a multi-use bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on animal cells or active components derived from animal cells.

A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on animal cells or active components derived from animal cells.

A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation and where the fermentation is based on animal cells or active components derived from animal cells.

A more preferred aspect of the present invention relates to a disposable bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on human cells or active components derived from human cells.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on human cells or active components derived from human cells.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in the lower part of the reactor, and where one compartment is the compartment where the fermentation takes place and one compartment is where foam is transported back to the fermentation mixture in the form of liquid based on gravitation and where the fermentation is based on human cells or active components derived from human cells.

A more preferred aspect of the present invention relates to a multi-use bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on human cells or active components derived from human cells.

A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on human cells or active components derived from human cells.

A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation and where the fermentation is based on human cells or active components derived from human cells.

A more preferred aspect of the present invention relates to a disposable bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on plant or insect cells or active components derived from plant or insect cells.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on plant or insect cells or active components derived from plant or insect cells.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation and where the fermentation is based on plant or insect cells or active components derived from plant or insect cells.

A more preferred aspect of the present invention relates to a multi-use bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on plant or insect cells or active components derived from plant or insect cells.

A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on plant or insect cells or active components derived from plant or insect cells.

A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation and where the fermentation is based on plant or insect cells or active components derived from plant or insect cells.

Another even more preferred aspect of the present invention relates to a steel bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on bacteriophage, bacteriophage host cells or active components derived from bacteriophage or bacteriophage host cells.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on bacteriophage, bacteriophage host cells or active components derived from bacteriophage or bacteriophage host cells.

A more preferred aspect of the present invention relates to a disposable bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on bacteriophage cells or active components derived from bacteriophage cells.

A more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation and where the fermentation is based on bacteriophage or bacteriophage host cells or active components derived from bacteriophage or bacteriophage host cells.

A more preferred aspect of the present invention relates to a multi-use bioreactor for fermentation characterized by comprising of at least two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on bacteriophage cells or active components derived from bacteriophage cells.

A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is based on bacteriophage and bacteriophage host cells or active components derived from bacteriophage or bacteriophage host cells.

A more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation and where the fermentation is based on bacteriophage or bacteriophage host cells or active components derived from bacteriophage or bacteriophage host cells.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is an anaerobic process.

Another even more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is an anaerobic process.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is an aerobic process.

Another even more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation is an aerobic process.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one chemical compound for use as drug substance in pharmaceutical product.

Another even more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation at least one chemical compound for use as drug substance in pharmaceutical product.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one chemical compound for use as starting material for production of drug substance in pharmaceutical product.

Another even more preferred aspect of the present invention relates to a multiple-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation at least one chemical compound for use as starting material for production of drug substance in pharmaceutical product.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one chemical compound for use as drug substance or for use as starting material for production of drug substance in pharmaceutical product where the drug substance is a protein or a protein derivative.

Another even more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one chemical compound for use as drug substance or for use as starting material for production of drug substance in pharmaceutical product where the drug substance is a protein or a protein derivative.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one chemical compound for use as drug substance or for use as starting material for production of drug substance in pharmaceutical product where the drug substance is a non-protein or a non-protein derivative.

Another even more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one chemical compound for use as drug substance or for use as starting material for production of drug substance in pharmaceutical product where the drug substance is a non-protein or a non-protein derivative.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one living organism for use in a pharmaceutical product.

Another even more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one living organism for use in a pharmaceutical product.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one chemical compound for use as drug substance or for use as starting material for production of drug substance in pharmaceutical product where the drug substance is for use in a pharmaceutical product for treatment of infections, cancer or an immunological disease.

Another even more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one chemical compound for use as drug substance or for use as starting material for production of drug substance in pharmaceutical product where the drug substance is for use in a pharmaceutical product for treatment of infections, cancer or an immunological disease.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one living organism for use in a pharmaceutical product for treatment of infections, cancer or an immunological disease.

Another even more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the fermentation produces at least one living organism for use in a pharmaceutical product for treatment of infections, cancer or an immunological disease.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the reactor is a gas-lift reactor.

Another even more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the reactor is a gas-lift reactor.

Another even more preferred aspect of the present invention relates to a disposable bioreactor for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid where the loss of product is at least reduced by a factor of 2 compared with the loss of product using a classical one-compartment reactor for the same process.

Another even more preferred aspect of the present invention relates to a multi-use bioreactor for fermentation characterized by comprising of two compartments where the compartments are separated by a wall that is absent or permeable for foam in the upper part of the reactor and is absent or permeable for liquid in a lower part of the reactor and where one compartment is the compartment where the fermentation takes place and one compartment is where foam is transported back to the fermentation mixture in the form of liquid where the loss of product is at least reduced by a factor of 2 compared with the loss of product using a classical one-compartment reactor for the same process.

Additional embodiments are described herein.

BRIEF DESCRIPTION OF THE FIGURES

FIG. 2 shows vertical cross sections of schematic drawings of four different exemplary bioreactor embodiments of the present disclosure comprising two compartments. In the drawings the flow of foam is illustrated by white arrows and return of foam to the fermentation chamber in the form of liquid is illustrated by black arrows.

FIG. 8 shows another embodiment of a bioreactor according to the present disclosure with a central separator shown in cross-section.

DETAILED DESCRIPTION OF THE INVENTION

Figure 1:
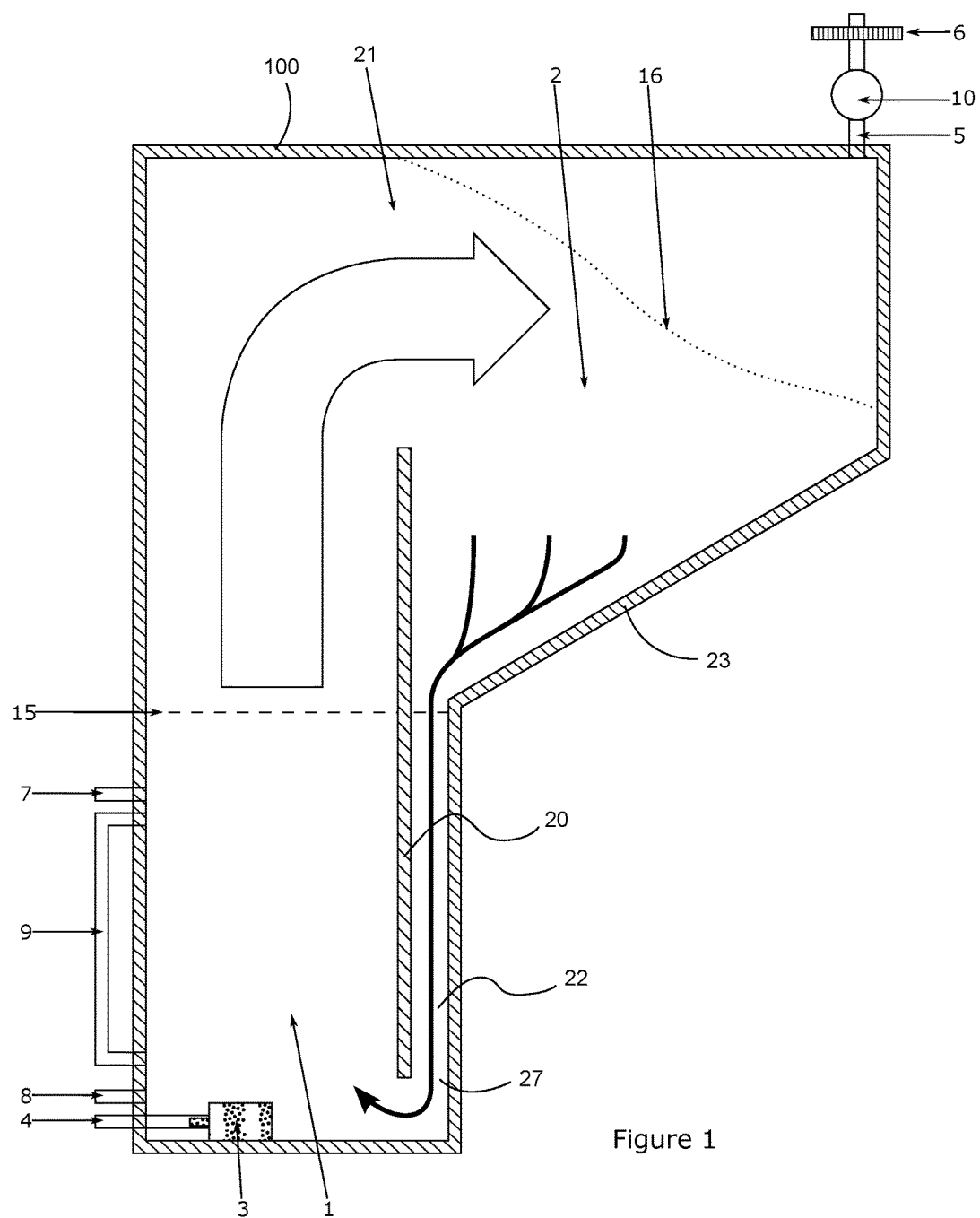
FIG. 1 shows a vertical cross section of a schematic of an exemplary bioreactor of embodiments of the present disclosure comprising two compartments. In the figure, the principle of how liquid is recycled from foam and returned to the fermentation chamber is demonstrated by a white arrow indicating direction of foam flow and by black arrows indicating liquid flow.

The present invention relates to the field of fermentation. More precisely it relates to a method and apparatus for production of products by use of living cells or active components derived from such cells using a bioreactor having a built in gas distributor and a specific system/device for handling foam formed in the process.

Bioreactors can be divided into 2 groups depending upon mode of operation; (1) a batch reactor, where the components are mixed or added over time and the product is produced in batches of various sizes and (2) flow reactors which carry material as a flowing stream where reactants are continuously fed into the reactor and there is a continuous production of products. The embodiments described here can be used for either mode of operation.

Bioreactors can also be divided into 2 groups depending upon the intended use; disposable reactors or single use reactors and reactors intended for production of multiple batches (multi-use). The disposable reactors have advantages related to cost and lack of need of cleaning and might therefore have advantages related to regulatory production of pharmaceuticals. Such reactors are typically produced in plastic materials. Different disposable, single use bioreactors are commercially available in different sizes. Classical multi-use bioreactors are typically made of stainless steel and are also commercially available from various suppliers. Although the embodiments described here can be used for either single use or multi-use, they are particularly well suited for single use as disposable reactors. It is possible for the reactors described here to be adapted for positioning inside, and used with, existing support systems for traditional single use bioreactors without separate zones for foam handling (e.g. single use bioreactors for growth of mammalian, fungal and insect cells).

A bioreactor typically comprise of the following components: a reactor tank, a thermal jacket, an agitation system, inlet openings with piping, outlet opening with piping, gas inlet system(s), gas outlet system(s) and detectors or sensors. The volume of the reactor tank can vary from less than one liter to several thousand liters. The agitation system can be in the form of mechanical agitation or gas-based agitation. Cell-based media and other biological systems are generally sensitive to mechanical stress. It is therefore an advantage to use gas bubbles for improving the mixing of the components in the reactor. The gas is usually introduced at the bottom of the reactor and the gas bubbles mix the components as a result of their transport to the surface of the reactor content. These reactors can be called gas-lift reactors. In addition to the physical mixing function of the gas in a gas-lift reactor, the gas might also be of nutrition value for the living cells. Typical gases used in bioreactors are oxygen, carbon dioxide, nitrogen and gas mixtures such as air. The gas is generally purified gas free from contaminants; especially biological contaminants like bacteria and virus. The function of the thermal jacket is to keep the reaction temperature at optimal level. The inlet openings are used to add components to the reaction mixture. The outlet openings can be at the bottom of the reactor, to withdraw liquid samples from the reactor or empty the reactor after the process has been finished, or at the top of the reactor to eliminate gases, typically carbon dioxide and excess of added gases. Outlet openings for withdrawal of liquid can also be at the top of the reactor to allow for removal of the finished fermentation mixture from the top. This might be done to reduce the amount of cells or cell debris removed from the reactor. The detectors and sensors are present to monitor critical parameters such as temperature, cell density, gas pressure, $CO_2$, $O_2$, pH, etc.

A bioreactor can be used for very many different processes. Each process is different with regard to reaction conditions. The fermentation process taking place in the bioreactor is highly dependent on the physical and chemical reaction conditions. These conditions include: nature of the cells or cell components responsible for the catalytic activity for the process, the overall composition of the broth/growth media/reaction media (raw materials and other chemical and biological components in reaction mixture), composition and amount of gas used, additives, temperature, osmolality, batch size and reactor parameters like geometry, composition and function.

Some biochemical processes taking place in bioreactors are anaerobic while others are aerobic. An anaerobic biochemical process is a process involving anaerobic organism that does not require oxygen for growth. The organism may react negatively or even die if oxygen is present.

An aerobic biochemical process is a process involving aerobic organism that can survive and grow in an oxygenated environment.

Various processes and apparatus for biochemical productions are known in the art and described in (e.g., EP1602715, U.S. Pat. No. 6,191,913, EP0343885, U.S. Pat. Nos. 6,245,555, 6,432,698, 6,709,862, 7,875,448, and 8,292,491. However, existing reactors have several major problems. One major problem when biochemical processes take place in bioreactors is the formation of foam. Foam is formed by trapping pockets of gas in a liquid and/or solid. In most foams, the volume of gas is large, with thin films of liquid and/or solid separating the regions of gas. Foam formation results in several problems in commercial biochemical production in bioreactors/fermenters. These problems include: inadequate mixing of the components in the reactor, clogging of gas outlet filters and loss of reaction volume/medium/liquid and/or product.

To overcome these problems various methods have been developed to prevent the formation of undesirable foam in a bioreactor or to remove the foam or the problems associated with the foam during the fermentation process and the following work-up of the fermented composition.

The classical solution to foam problem in biochemical processes taking place in bioreactors is to add an antifoaming agent like silicone chemicals often in combination with other chemicals.

The use of antifoaming agents in biochemical processes is described in several publications and patent documents including: Y. Kawase and M. Moo Young: The effect of antifoam agents on mass transfer in bioreactors in Bioprocess Engineering 5 (1990) page 169-173, Waheed A. Al-Masry: Effects of antifoam and scale-up on operation of bioreactors in Chemical Engineering and Processing: Process Intensification 38, Issue 3, (1999) page 197-201, S. Zhang, A. Handa and R. E. Spier: Foaming and media surfactant effects on the cultivation of animal cells in stirred and sparged bioreactors in Journal of Biotechnology 25, Issue 3, (1992), page 289-306, J. Bryant: Chapter VII Anti-Foam Agents in Methods in Microbiology 2, (1970), page 187-203, EP 0 391 590, describing the use of an oil-based material encapsulated in a water-soluble granule antifoam agent and DE 41 42 967 which describes introducing a liquid antifoam agent directly onto and/or into the foam itself.

However, these chemicals are costly, might plug filters, and might affect mass in the biochemical process and oxygen transfer in the reactor system. The antifoam chemicals might in addition be toxic to the cells and thereby reduce the yield of the process. Another problem is that addition of these chemicals might result in difficult and costly purification processes of the product and, if the product is intended for use in a pharmaceutical agent, might represent regulatory challenges for final approval of the desired product.

Another method for solving the problem is to use a mechanical device and foam detectors. Such devices are described in the following documents: U.S. Pat. No. 5,612,219, US2008/0068920, US2012/0132548, US2013/0039810, U.S. Pat. No. 6,673,599, CN201520758, US2003068813, GB951674, WO0078916, and DE4142967. Mechanical anti-foaming devices typically operate by wiping or beating the foam to break down the gas pockets. These devices add complexity to the system as they need to be positioned within the reactor and powered. They also add cost and are not well suited to disposable, single use reactors.

Embodiments of the present disclosure provide improved bioreactors that address these problems. Specifically, in some embodiments, the present invention provides a method and apparatus (e.g., bioreactor (fermenter)) for production of products by use of living cells or active components derived from such cells using a bioreactor characterized by comprising of at least two compartments where the compartments are separated by a wall that is absent or permeable for foam in the upper part of the reactor and is absent or permeable for liquid in a lower part of the reactor, and where at least one compartment is the compartment where the fermentation takes place and at least one compartment is where foam is transported back to the fermentation mixture in the form of liquid.

Embodiments of the present invention provide a bioreactor for fermentation characterized by comprising of at least two compartments where the compartments are separated by a wall that is absent or permeable for foam in the upper part of the reactor and is absent or permeable for liquid in a lower part of the reactor, and where at least one compartment is the compartment where the fermentation takes place and at least one compartment is where foam settles, is stored and transported back to the fermentation mixture in the form of liquid.

Embodiments of the present invention provide a bioreactor for fermentation characterized by comprising of at least three compartments where at least one compartment is the fermentation compartment, at least one compartment is the foam handling compartment where foam is transported back to the fermentation mixture in the form of liquid and at least one compartment is the waste compartment, and where the fermentation compartments and the foam handling compartments are separated by walls which are absent or permeable to foam in the upper part of the reactor and absent or permeable to liquid in a lower part of the reactor, and where foam handling compartments and waste compartments are separated by walls which are absent or permeable for foam in the upper part of the reactor.

In some embodiments, the bioreactor comprises at least two (e.g., three or more, four or more, etc.) of each type of compartment.

In some embodiments, the bioreactor comprises at least two compartments separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid.

Exemplary reactors are shown in FIGS. 1-8. In the Figures and below description, the following numbers are used to describe the following exemplary components: 1 Fermentation chamber, i.e. fermentation compartment; 2 Foam chamber, i.e. foam compartment; 3 Gas sparger; 4 Gas inlet; 5 Gas outlet; 6 Gas outlet filter; 7 One or more inlets;

8 One or more outlets; 9 One or more culture monitor loops; 10 Gas pressure control device; 11 Foam transfer component; 12 Culture return component; 13 agitation or mixing means, e.g. a magnetic propeller; 14 Foam restricting component, i.e. wall, (which may be permeable to liquid); 15 Stapled line indicates exemplary liquid level in fermentation chamber; 16 Dotted line indicates exemplary foam level in foam chamber; 17 Waste chamber, i.e. waste compartment.

Figure 4:
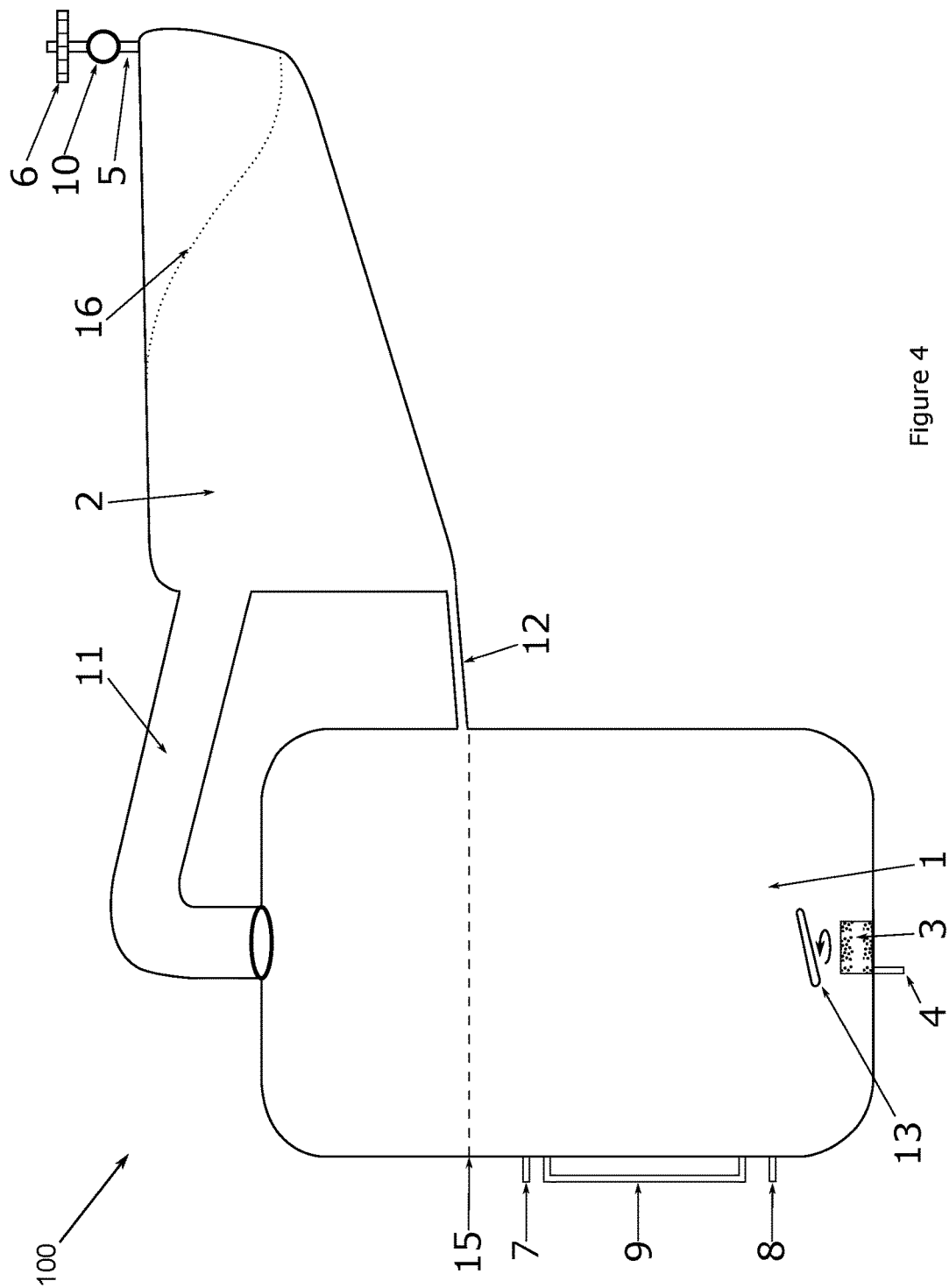
FIG. 4 shows a vertical cross-section of a schematic of an exemplary bioreactor of embodiments of the present disclosure comprising two compartments.
Figure 5:
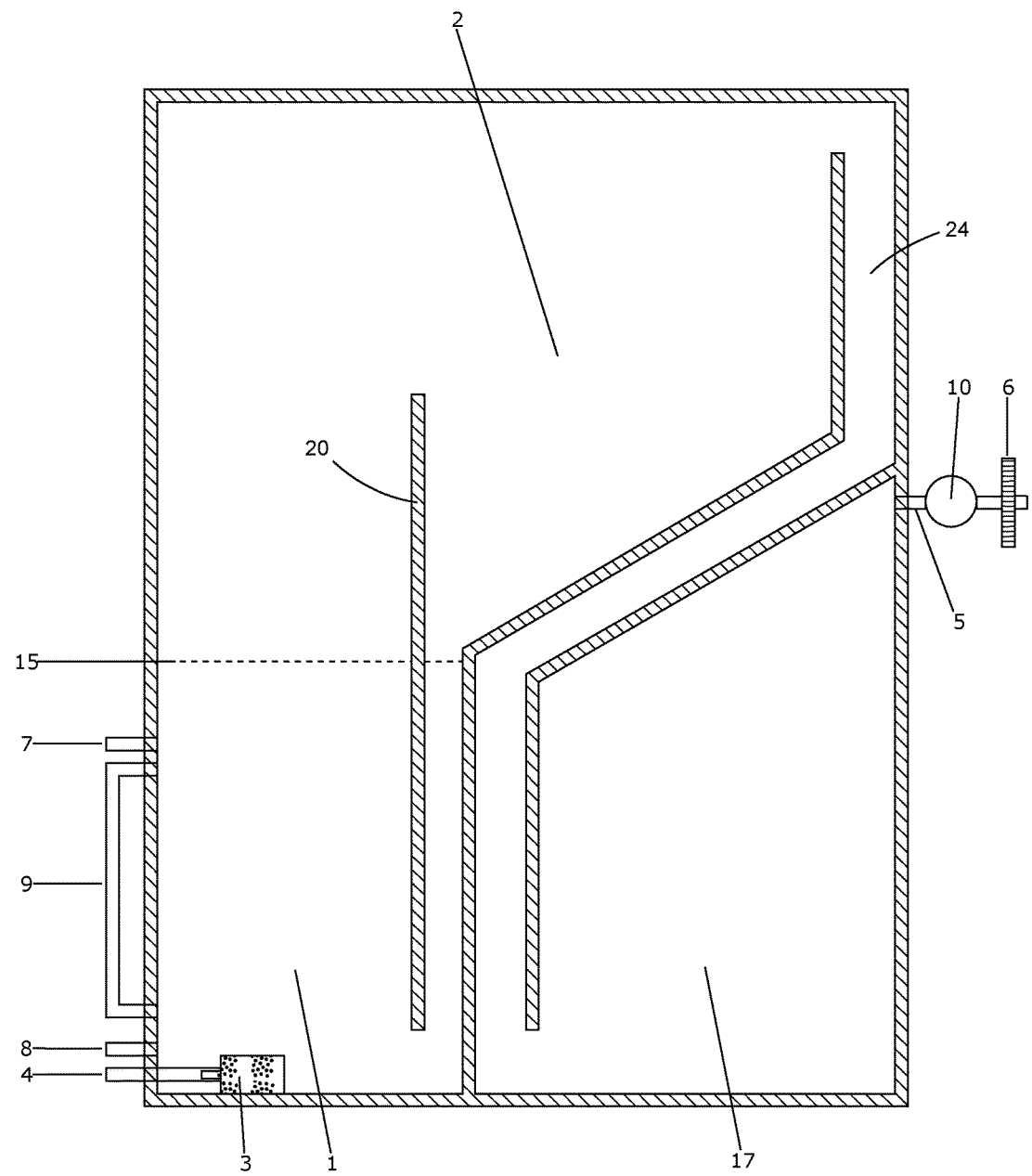
FIG. 5 shows a vertical cross-section of a schematic of an exemplary bioreactor of embodiments of the present disclosure comprising three compartments.
Figure 6:
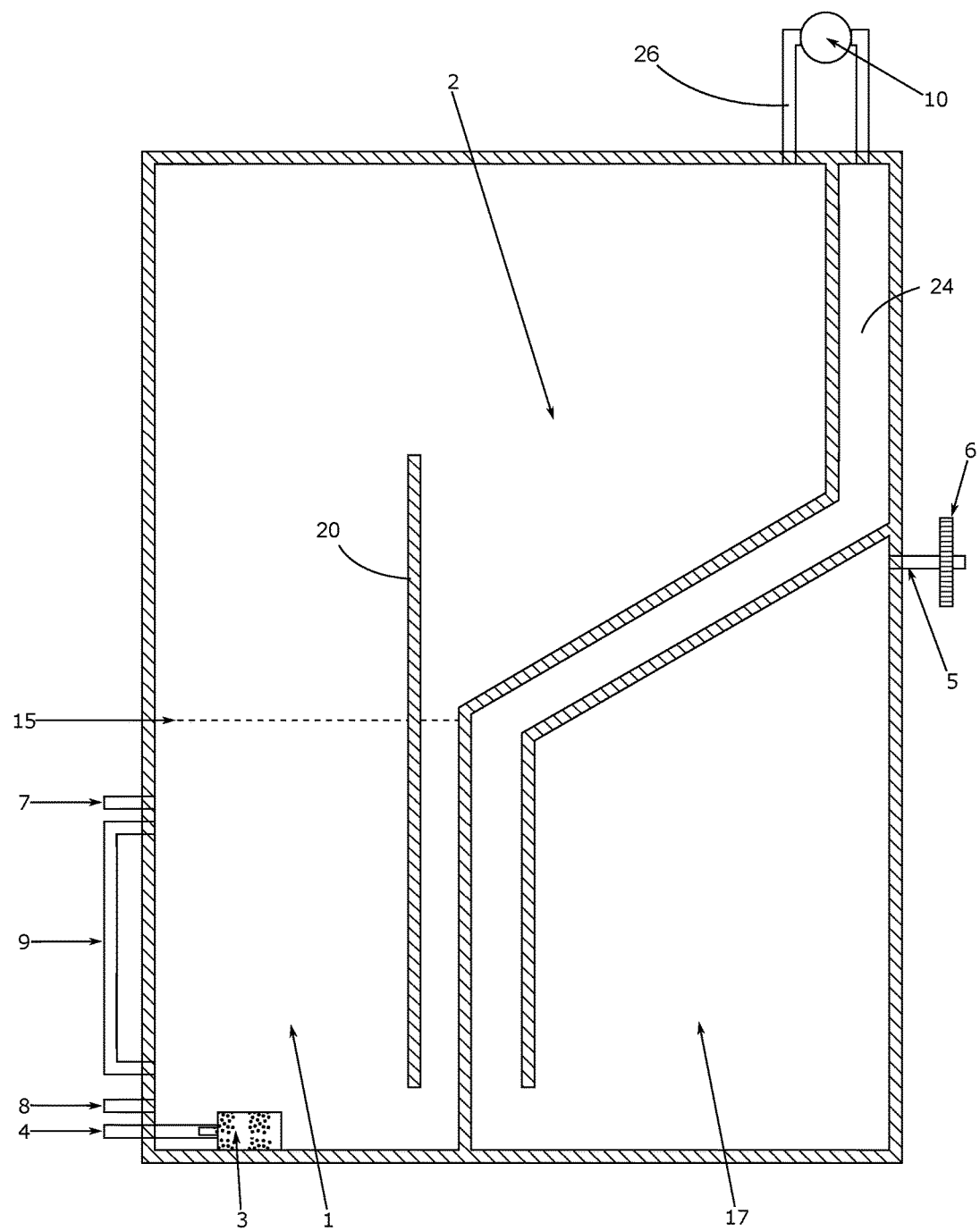
FIG. 6 shows a vertical cross-section of a schematic of an exemplary bioreactor of embodiments of the present disclosure comprising three compartments.

In some embodiments, the reactor comprises a fermentation chamber 1 and a foam chamber 2. In some embodiments, the reactor comprises a gas sparger 3 and gas inlet 4. In some embodiments, the reactor comprises a gas outlet 5, a gas outlet filter 6 and a gas pressure control device 10. In some embodiments, the gas outlet filter 6 and a pressure control 10 are on the same assembly as shown in FIGS. 1-5. In other embodiments, they are in different locations on the reactor (e.g., as shown in FIG. 6). In some embodiments, the reactor comprises one or more inlets 7, one or more outlets 8 and one or more culture monitoring loops 9. In some embodiments they are located on the side of the reactor, in other embodiments they are in different locations, e.g. on the top or the bottom of the reactor. In some embodiments, the bioreactor comprises a foam transfer component 11 and a culture transfer return 12. In some embodiments, the bioreactor comprises agitation or mixing means, e.g. a magnetic propeller 13. In some embodiments, the fermentation chamber 1 and the foam chamber 2 is partly separated by a foam restricting component permeable to liquid 14, as shown in FIG. 2. In some embodiments, the bioreactor comprises a waste chamber 17 for example as shown in FIGS. 5 and 6. In some embodiments, foam is transported back to the fermentation mixture in the fermentation chamber in the form of liquid based on gravitation. One advantage related to the present method and apparatus is that it is flexible and scalable. The reactor size is preferably between 100 ml and 100 $m^3$, more preferably between 1 liter and 50 $m^3$, even more preferably between 2 liter and 20 $m^3$, most preferably between 4 liter and 10 $m^3$.

Another advantage is that there is no need for mechanical anti-foaming devices nor chemical anti-foaming agents. A preferred aspect of the present invention relates to a process free from both mechanical anti-foam devices and chemical anti-foam agents.

In some embodiments, the apparatus comprises one or more systems for mixing of components.

More specifically, FIG. 1 shows a reaction chamber 100 with a fermentation chamber 1 (fermentation zone) at a lower part of the reaction chamber 100. The dashed line 15 indicates the normal liquid level that will be present in the fermentation chamber 1. This liquid may be fed into the reaction chamber 100 via one or more inlets 7 and may be extracted from the reaction chamber 100 via one or more outlets 8. Fermentation may be performed in batches or may be performed on a continuous basis with continuous extraction and with new culture medium continually being fed in to replace the extracted fluid. Culture monitoring loop(s) 9 can be used to measure various parameters of the culture or fermentation mixture such as temperature, cell density, gas pressure, $CO_2$, $O_2$, pH, etc. which may be useful for monitoring and controlling the reaction. Gas sparger 3 (supplied with gas from gas inlet 4) is located at the bottom of the fermentation zone and emits gas bubbles into the liquid which rise up through the liquid causing aeration as well as mixing.

During the reaction, foam is produced above the fermentation zone 1. A vertical wall 20 forms a barrier parallel to a wall of the reaction chamber 100. As indicated by the white arrow in FIG. 1, the foam initially rises upwards, constrained by wall 20, then upon reaching the top of wall 20, passes above the wall 20 through a large aperture 21 formed between the top of the wall 20 and the top of the reaction chamber 100. The foam thus enters the foam settling chamber 2. The typical level of foam in the reaction chamber 100 is indicated by dotted line 16. The wall 20 partially separates the foam settling chamber 2 from the fermentation chamber 1 and thus largely isolates the foam settling chamber 2 from the turbulent activity of the fermentation chamber 1 (e.g. caused by agitation and/or rising gas bubbles from the gas sparger 3). Isolated from this activity, the foam can settle and return to liquid form as indicated by the black arrows in FIG. 1. The wall 20 extends across part of the foam chamber 2 and also extends into the fermentation chamber 1 and forms a passage 22 between itself and the wall of the fermentation chamber 1. The channel 22 is relatively small (narrow) and feeds the returning liquid through a small aperture 27 to a lower portion of the fermentation zone 1 so that no foam can rise up the aperture 27 and the passage 22 to interfere with the settling process. The lower wall 23 of foam chamber 2 is sloped so as to encourage liquid to flow towards passage 22 and back to fermentation chamber 1 under gravity.

A gas outlet 5 with gas pressure control 10 and gas outlet filter 6 are provided at the top of the reaction chamber 100 at the far corner of the expanded region that forms the foam settling chamber 2. As can be seen from the dotted line 16 that represents the normal expected foam level, the gas outlet 5 and filter 6 are positioned as far as possible from the foam so that clogging of the outlet 5 or wetting of the filter 6 will not occur until the reaction chamber 100 is completely filled with foam.

FIG. 2 shows four different variations of the reactor shown in FIG. 1. FIG. 2a is identical to FIG. 1. FIG. 2b differs in that the wall 20b does not extend into the fermentation chamber 1, but instead extends partly across the divide between the fermentation chamber 1 and the foam chamber 2, leaving a large aperture 21b at the top to allow foam to enter the foam chamber 2 and a smaller aperture 27b at the bottom that allows liquid to drain out of the foam chamber 2 back into the fermentation chamber 1. The small aperture 27b must be small enough that foam cannot enter into foam chamber 2 and disturb the settling process. It will be appreciated that while FIG. 2b shows the wall 20b vertical and parallel to the sides of the fermentation chamber 1, it need not be so. Instead, wall 20b could be angled so as to make the foam settling chamber 2 wider at the top, thus providing more room for settling. A similar modification could also be made to the wall 20 of FIG. 2a.

FIG. 2c is similar to FIG. 2b except that in place of wall 20b, a foam restricting component 14 is provided. The foam restricting component may be a material that is impermeable to foam, but permeable to liquid such as a fabric or fine mesh. Being impermeable to foam, the foam restricting component 14 can adjoin the main wall of the reaction chamber 100, i.e. there is no need to form a small aperture or passage 22, 27, 27b as liquid can pass relatively easily back to the fermentation chamber 1, while foam is readily prevented from entering the bottom of the settling zone 2 and interfering with the settling process.

FIG. 2d is the same as FIG. 1 (and FIG. 2a), but with no wall 20. This embodiment has less separation between the foam settling zone 2 and the fermentation zone 1 and therefore may not be suitable for all reactions, but for some situations the separation that is achieved simply by providing the settling zone 2 to the side of the fermentation zone 1 is sufficient to encourage settling and reduce the overall foam volume within the reaction chamber 100.

Figure 3:
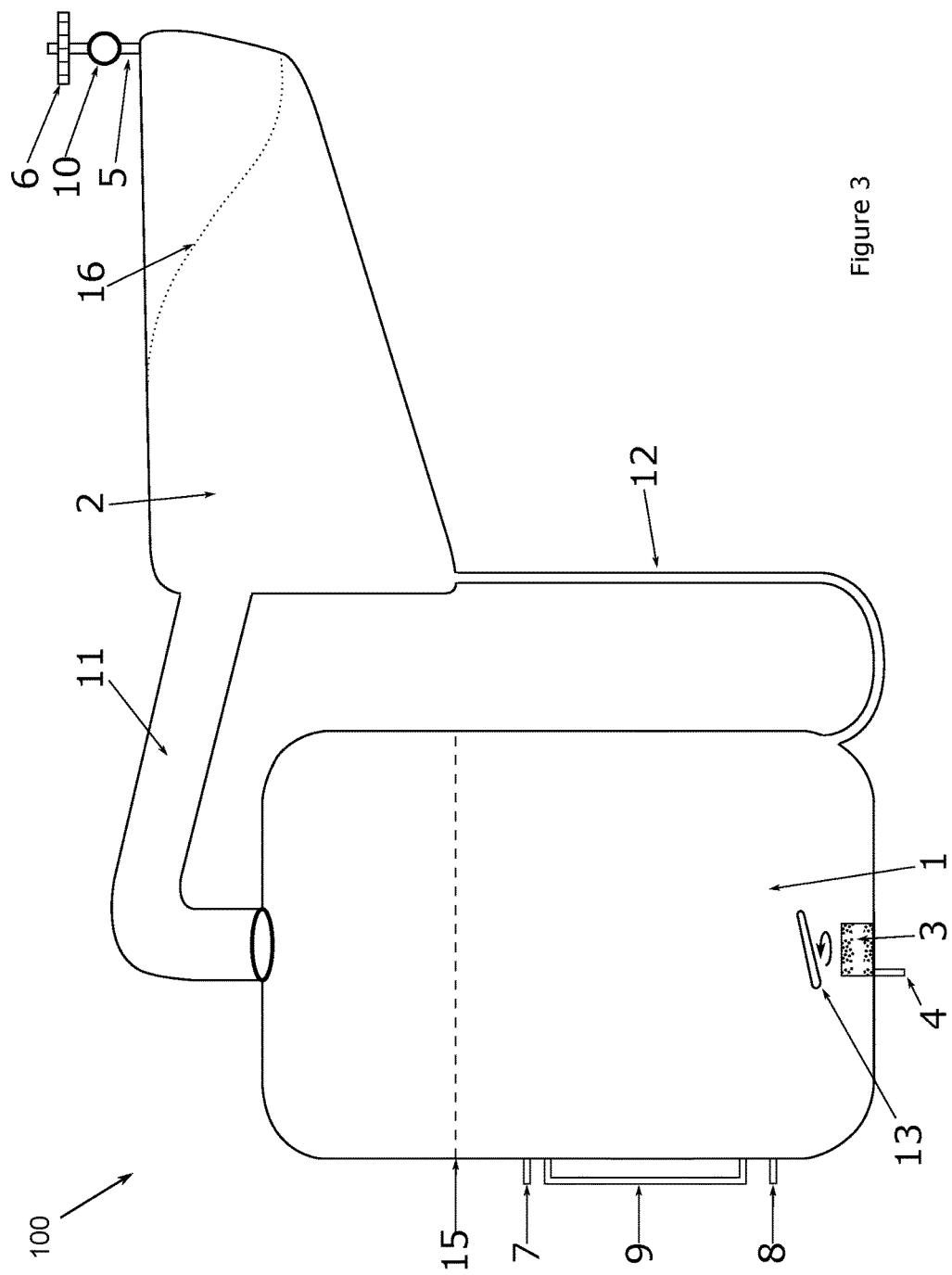
FIG. 3 shows a vertical cross-section of a schematic of an exemplary bioreactor of embodiments of the present disclosure comprising two compartments.

FIG. 3 shows an embodiment where the foam settling chamber 2 is formed separately from the fermentation chamber 1. The connections between the two chambers 1, 2 are formed by two conduits. Foam transfer component 11 is a conduit of relatively large diameter sufficient to transfer foam from the top of the fermentation chamber 1 into the top of the foam settling chamber 2. Culture return component 12 is a conduit of relatively small diameter for transferring settled foam (i.e. liquid) back to the fermentation chamber 1. In FIG. 3 the culture return component 12 feeds back to a lower portion of the fermentation chamber 1. FIG. 4 is a variation of FIG. 3 in which the culture return component 12 feeds back to an upper portion of the fermentation chamber 1. Although the fermentation chamber 1 and foam settling chamber 2 are formed as separate chambers, together they are still considered to form a single reaction chamber 100, i.e. a single bioreactor.

FIG. 5 shows a reactor similar to that of FIG. 1, but with the addition of a waste chamber 17. The waste chamber 17 is connected to the foam settling chamber 2 via a conduit 24 that extends from an upper part of the foam chamber 2 to a lower part of the waste chamber 17. The gas outlet 5 and filter 6 are connected to the waste chamber 17 rather than to the foam chamber 2, thus escaping gas must pass first through the foam chamber 2, then through conduit 24 and through waste chamber 17 before leaving the reaction chamber 100 through gas outlet 5. In normal operation, foam will collect and settle on foam chamber 2 and return under gravity to the fermentation chamber 1. However, if excess foam is produced for some reason, e.g. due to process variations, any excess foam that cannot be accommodated in foam chamber 2 will pass through conduit 24 and into waste chamber 17 where it will eventually settle. There is no exit from waste chamber 17 for settled foam, so it simply collects there and is discarded when the fermentation process has been completed. As the waste chamber is only for temporary overflows, it has been found that very little of the fermentation mixture overflows and thus very little product is wasted in this manner.

Figure 7:
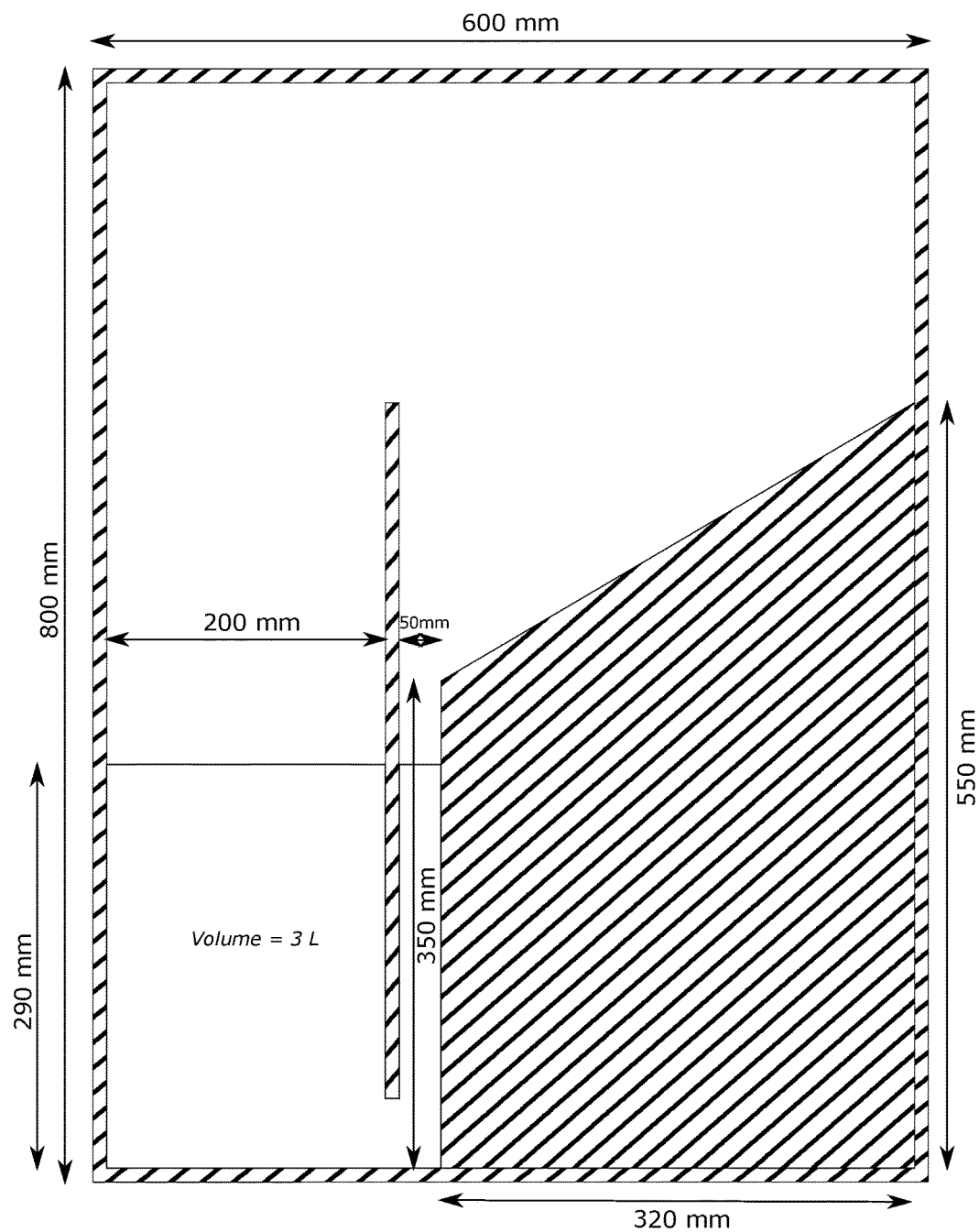
FIG. 7 shows a vertical cross-section and dimensions of a schematic of an exemplary bioreactor of embodiments of the present disclosure which comprises sheets of plastic (HDPE300) welded together to form two compartments. The hatched area in the figure indicates where the two sheets of plastic are welded together.

It can be seen that the waste chamber 17 is situated below the foam chamber 2 in a location which is otherwise unused by the reaction chamber 100. One particularly convenient method of forming a reaction chamber 100 as shown in FIGS. 1, 2 and 5 to 7 is to place two flat, flexible plastic sheets on top of one another (i.e. overlapped) and to weld them together so as to form the chambers as depicted. As such sheets of plastic are typically provided in a rectangular shape, the waste chamber 17 conveniently uses a space that would otherwise be wasted. As an example, FIG. 7 shows the welds that would be used to from a reaction chamber 100 of FIG. 1 (the hatched portions show the welds). It can be seen that the whole of the area that would be occupied by the waste chamber 17 has been welded.

FIG. 6 is a variation of the embodiment of FIG. 5. Instead of the conduit 24 being open to the foam chamber 2 at the top, a separate connection 26 is provided outside the main reaction chamber 100 to link the foam chamber 2 to the conduit 24. Once the foam chamber 2 is filled, further excess foam will pass through connection conduit 26 into conduit 24 and into waste chamber 17. The gas pressure control device 10 is provided in this connection 26 and can be used to control the pressure within the fermentation chamber 1 and foam chamber 2. Increasing the pressure here can reduce the volume of foam being generated and prevent or reduce overflow into the waste chamber 17, thus resulting in less wastage overall.

FIG. 7 shows some typical dimensions for a reactor of FIG. 1 designed for using 3 litres of culture medium. It will be appreciated that these dimensions and volumes are not intended to be limiting.

FIG. 8a shows an alternative construction for a reaction chamber 200. Instead of forming the reaction chamber 200 from two flat sheets, the chamber 200 is formed from one or more cylindrical tubes (which may themselves be formed from thin plastic sheets) with an insert 210 provided in the middle and welded (or otherwise fixed) to walls of the reaction chamber 200. The insert 210 divides the reaction chamber 200 into a fermentation chamber 1 and a foam settling chamber 2. In this embodiment, the foam settling chamber 2 is directly above the fermentation chamber 1 rather than laterally displaced, but it is separated from the activity of the fermentation chamber 1 by the separator insert 210. The insert 210 is shown in horizontal cross-section in FIG. 8b and in vertical cross-section in FIG. 8c.

Separator 210 has a greater thickness (in the height dimension of the reactor) on one side than on the other side and is provided with a large through hole 211 in the form of a tube for foam to pass from the reaction chamber 1 into the foam settling chamber 2. This tube 211 is positioned off centre in the separator 210 and extends through the thicker part of the separator 210 so that a settling zone 220 is formed to the side of the tube 211 in the foam chamber 2. Thus, foam is fed into the foam chamber 2 at a position higher than the settling zone 220 so that the rising foam does not interfere with the settling process in the settling zone 220. A smaller return passage 212 is formed through the thinner side of the insert 210 for return of liquid form the settling zone 220 to the fermentation chamber 1. The passage 212 is sloped so as to direct liquid at the wall of the fermentation chamber 1 so that it will flow down the wall rather than drip back into the fermentation chamber 1.

The horizontal cross-sectional shape of the insert 210 shown in FIG. 8b is in the form of a figure-of-eight with two bulging areas connected by a narrow neck (the bulge around the foam tube 211 being much larger than the bulge around the liquid return passage 212). The separator insert 210 is made from a harder, rigid plastic so that when the main reactor walls are made from thin, flexible plastic sheet and welded around the insert 210, they conform locally to the shape of the insert. This forms the reactor walls partially into a tube around the liquid return passage 212 and further hinders foam from rising upwards through that passage 212. However, it should be noted that this cross-sectional shape is only one example and is not necessary for the functioning of the insert 210 which may equally well be formed with an oval or circular horizontal cross-section so that the reactor has the same (or very similar) profile throughout the majority of its height.

As can be seen in FIGS. 8a and 8c, the inlet tubes 7 may be formed integrally with the separator insert 210, e.g. on a downwardly projecting lip 213. This facilitates manufacture as it is easier to form watertight seals and structures on the more rigid plastic of the insert than it is to form those inlets 7 directly on the thinner reactor chamber wall.

A preferred aspect of the present apparatus and methods is related to a bioreactor where the components are mixed by gas bubbles rising through the fermentation mixture from the gas sparger preferably placed at the bottom of the reactor (gas-lift reactor).

Another preferred aspect of the present apparatus and methods is related to a bioreactor where the components are mixed with physical methods like for example agitation or steering. If physical methods are used for mixing the methods are preferably methods that do not disturb the cellular function. Such methods include typically very careful stirring using magnetic stirring bars and very careful agitation.

The choice of which system to use for a particular mixture is dependent on several parameters, including type and size of reactor, type of cell, organism, microorganism and active component derived from such cells or organisms and product to be produced.

For some processes there might be an advantage to combine two mixing methods, preferably gas-lift and a physical method selected from a careful stirring method or a careful agitation method.

A preferred aspect of the present invention is an apparatus and method related to a disposable bioreactor as previously described where the reactor is sterile.

A preferred aspect of the present invention is an apparatus and method related to a disposable bioreactor as previously described where the reactor is sterile and packed in an outer container to keep the reactor sterile until use.

A further preferred aspect of the present invention is an apparatus and method related to a disposable bioreactor as previously described where the reactor is sterile and packed in an outer container to keep the reactor sterile until use and where the reactor with outer container is sterilized by heat or radiation.

An even more preferred aspect of the present invention is an apparatus and method related to a disposable bioreactor as previously described where the reactor is sterile and packed in an outer container to keep the reactor sterile until use and where the reactor with outer container is sterilized by gamma radiation.

Another preferred aspect of the present invention is an apparatus and method related to a disposable bioreactor as previously described where the reactor can be sterilized by the end user.

In some embodiments, the fermentation is based on bacterial cells or active components derived from bacterial cells.

In some embodiments, fermentation is based on fungal cells or active components derived from fungal cells, animal cells (e.g., human cells) or active components derived from animal cells, plant or insect cells or active components derived from plant or insect cells, bacteriophage, bacteriophage host cells or active components derived from bacteriophage or bacteriophage host cells.

In some embodiments, the fermentation is based on bacterial cells or active components derived from bacterial cells, fungal cells or active components derived from fungal cells, animal cells (e.g., human cells) or active components derived from animal cells, algae or active components derived from algae, protists or active components derived from protists, plant cells or active components derived from plant cells, or insect cells or active components derived from insect cells.

In some embodiments, the fermentation is based on bacteriophage and bacteriophage host cells or active components derived from bacteriophage or bacteriophage host cells.

In some embodiments, fermentation is an aerobic process. In some embodiments, fermentation is an anaerobic process.

Embodiments of the present disclosure further provide systems comprising the bioreactors described herein and one or more additional reagents or apparatuses useful in fermentation (e.g., reagents, microorganisms, analytical equipment, etc.).

The bioreactors described herein find use in the production of a variety of products. Examples include, but are not limited to, chemical compounds (e.g., for use as drug substance in pharmaceutical product or as a starting material for production of drug substance in pharmaceutical product). In some embodiments, the drug is a protein or protein derivative or a non-protein or non-protein derivative. In some embodiments, the fermentation produces at least one living organism (e.g., for use in a pharmaceutical product).

In some embodiments, the drug product or living organism finds use in the treatment of infections, cancer or an immunological disease.

In some embodiments, the reactors described herein provide the advantage that the loss of product is at least reduced by a factor of 2 compared with the loss of product using a classical one-compartment reactor for the same process.

In some embodiments, the present invention provides systems and methods of utilizing the bioreactors described herein for the fermentation and production of a variety of cells, drugs, and drug precursors.

In some embodiments, the proteins and protein derivatives produced using the bioreactor and methods described in the present document include monoclonal antibodies and fragments of monoclonal antibodies for therapeutic and diagnostic use. The monoclonal antibodies can be murine, human, humanized or chimeric antibodies or antibody conjugates. Some examples of monoclonal antibodies and fragments thereof include abagovomab, abciximab, actoxumab, adalimumab, adecatumumab, aducanumab, afelimomab, afutuzumab, alacizumab pegol, alemtuzumab, alirocumab, altumomab pentetate, amatuximab, anatumomab mafenatox, anifrolumab, anrukinzumab, apolizumab, arcitumomab, aselizumab, atinumab, atlizumab, atorolimumab, bapineuzumab, basiliximab, bavituximab, bectumomab, belimumab, benralizumab, bertilimumab, besilesomab, bevacizumab. bezlotoxumab, biciromab, bimagrumab, bivatuzumab mertansine, blinatumomab, blosozumab, brentuximab vedotin, briakinumab, brodalumab, canakinumab, cantuzumab mertansine, cantuzumab ravtansine, caplacizumab, capromab pendetide, carlumab, catumaxomab, cedelizumab, certolizumab pegol, cetuximab, citatuzumab bogatox, cixutumumab, clazakizumab, clenoliximab, clivatuzumab tetraxetan, conatumumab, concizumab, crenezumab, dacetuzumab, daclizumab, dalotuzumab, daratumumab, demcizumab, denosumab, detumomab, dorlimomab aritox, drozitumab, duligotumab, dusigitumab, ecromeximab, eculizumab, edobacomab, falizumab, efungumab, eldelumab, elotuzumab, elsilimomab, enavatuzumab, enlimomab pegol, enokizumab, enoticumab, ensituximab, epitumomab cituxetan, epratuzumab, erlizumab, ertumaxomab, etaracizumab, etrolizumab, evolocumab, exbivirumab, faralimomab, farletuzumab, fasinumab, felvizumab, fezakinumab ficlatuzumab, figitumumab, flanvotumab, fontolizumab, foralumab, Foravirumab, fresolimumab, fulranumab, futuximab, galiximab, ganitumab, gantenerumab, gavilimomab, gemtuzumab, gevokizumab, girentuximab, glembatumumab vedotin, golimumab, gomiliximab, guselkumab, Ibalizumab, ibritumomab tiuxetan, icrucumab, igovomab, imciromab, imgatuzumab, inclacumab, indatuximab, iravtansine, infliximab, intetumumab, inolimomab, minotuzumab ozogamicin, ipilimumab, iratumumab, itolizumab, ixekizumab, keliximab, labetuzumab, lambrolizumab, lampalizumab, lebrikizumab, lemalesomab, lerdelimumab, lexatumumab, libivirumab, ligelizumab, lintuzumab, lirilumab, lodelcizumab, lorvotuzumab mertansine, lucatumumab, lumiliximab, mapatumumab, margetuximab, maslimomab, mavrilimumab, matuzumab, mepolizumab, metelimumab, milatuzumab, minretumomab, mitumomab, mogamulizumab, morolimumab, motavizumab, moxetumomab pasudotox, muromonab-CD3, nacolomab tafenatox, namilumab, naptumomab estafenatox, narnatumab, natalizumab, nebacumab, necitumumab, nerelimomab, nesvacumab, nimotuzumab, nivolumab bofetumomab merpentan, ocaratuzumab, ocrelizumab, odulimomab, ofatumumab olaratumab, olokizumab, omalizumab, onartuzumab, ontuxizumab, oportuzumab monatox, oregovomab, orticumab, otelixizumab, otlertuzumab, oxelumab, ozanezumab, ozoralizumab, pagibaximab, palivizumab, panitumumab, pankomab, panobacumab, parsatuzumab, pascolizumab, pateclizumab, patritumab, pemtumomab, perakizumab, pertuzumab, pexelizumab, pidilizumab, pinatuzumab vedotin, pintumomab, placulumab, polatuzumab vedotin, ponezumab, priliximab, pritoxaximab, pritumumab, quilizumab, racotumomab, radretumab, rafivirumab, ramucirumab, ranibizumab, raxibacumab, regavirumab, reslizumab, rilotumumab, rituximab, robatumumab, roledumab, romosozumab, rontalizumab, rovelizumab, ruplizumab, samalizumab, sarilumab, satumomab pendetide, secukinumab, seribantumab, setoxaximab, sevirumab, sibrotuzumab, sifalimumab, siltuximab, simtuzumab, siplizumab, sirukumab, solanezumab, solitomab, sonepcizumab, sontuzumab, stamulumab, sulesomab, suvizumab, tabalumab, tacatuzumab tetraxetan, tadocizumab, talizumab, tanezumab, taplitumomab paptox, tefibazumab, telimomab aritox, tenatumomab, teneliximab, teplizumab, teprotumumab, ticilimumab tildrakizumab, tigatuzumab, tocilizumab, toralizumab, tositumomab, tovetumab, tralokinumab, trastuzumab, tregalizumab, tremelimumab, tucotuzumab, celmoleukin, tuvirumab. ubituximab, urelumab, urtoxazumab, ustekinumab, vantictumab, vapaliximab, vatelizumab, vedolizumab, veltuzumab, vepalimomab, vesencumab, visilizumab, volociximab, vorsetuzumab mafodotin, votumumab, zalutumumab, zanolimumab, zatuximab, ziralimumab, zolimomab aritox Monoclonal antibodies can, according to the present invention be prepared in bioreactors for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation using well-known biochemical processes. Biochemical processes for production of monoclonal antibodies are for example described in the following documents: U.S. Pat. Nos. 8,658,774, 8,658,770, 8,658,386, 8,658,354, 8,652,470, 8,652,469, 8,637,032, 8,632,777, 8,628,778, 8,623,370, 8,623,368, 8,623,363, 8,618,262, 8,613,923, 8,609,818, 8,609,816, 8,609,096 8,604,174, 8,603,987, 8,603,469, 8,603,467, 8,598,321, 8,597,648, 8,591,891, 8,591,889, 8,586,042, 8,586,041, 8,580,259, 8,574,853, 8,574,581, 8,574,580, 8,568,723, 8,563,255, 8,551,486, 8,546,542, 8,540,996, 8,540,995, 8,540,991, 8,536,313, 8,536,312, 8,535,667, 8,535,639, 8,529,903, 8,529,902, 8,529,901, 8,524,870, 8,524,456, 8,524,233, 8,519,106, 8,519,104, 8,518,408, 8,518,407, 8,513,397, 8,513,391, 8,512,959, 8,507,207, 8,507,206, 8,506,963, 8,506,961, 8,501,471, 8,501,182, 8,496,937, 8,496,931, 8,492,529, 8,492,097, 8,491,903, 8,491,898, 8,491,895, 8,487,083, 8,487,082, 8,486,406, 8,486,401, 8,486,393, 8,481,039, 8,481,030, 8,476,033, 8,475,798, 8,470,326, 8,466,262, 8,461,308, 8,461,307, 8,460,891, 8,455,626, 8,450,464, 8,450,068, 8,449,887, 8,445,643, 8,445,219, 8,444,986, 8,440,797, 8,435,801, 8,431,686, 8,425,902, 8,420,093, 8,414,892, 8,409,573, 8,409,572, 8,404,820, 8,404,818, 8,404,817 and other older US patents identified by search in: www.uspto.gov based on the following search profile: TTL/(monoclonal AND (antibodies OR antibody)).

Other proteins and protein derivatives produced using the bioreactor and methods described in the present document include insulin and insulin derivatives. Typical such compounds include human insulin and human insulin analogues like for example insulin lispro, insulin aspart, insulin glulisine, glargine insulin, detemir insulin, insulin degludec.

Insulin and insulin analogues can, according to the present invention be prepared in bioreactors for fermentation characterized by comprising of two compartments where the compartments are separated by a wall that is absent or permeable for foam in the upper part of the reactor and is absent or permeable for liquid in a lower part of the reactor, and where one compartment is the compartment where the fermentation takes place and one compartment is where foam is transported back to the fermentation mixture in the form of liquid based on gravitation using well-known biochemical processes. Biochemical processes for production of insulin and insulin analogous are for example described in the following documents and references herein: U.S. Pat. Nos. 7,659,363, 7,396,903, 6,380,355, 5,986,048, 5,962,267, 5,700,662, 5,663,291, 5,506,202, 5,496,803, 5,457,066, 5,149,716, 5,122,603, 5,049,545, 4,639,332, 4,614,730, 4,601,979, 4,601,852, 4,489,159, 4,430,266, 4,421,685, 4,343,898, 4,332,893, 4,225,671, 4,215,037, 4,195,125, 4,085,204, 4,029,642, 4,029,641 4,014,861, 4,013,628, 3,945,988.

Other proteins and protein derivatives produced using the bioreactor and methods described in the present document include enzymes. These enzymes might be useful as drug substances, as industrial enzymes, enzymes for household use and for use in food or beverages or to produce such products. Enzymes are grouped into a numerical classification scheme based on the chemical reactions they catalyze. The system is called The Enzyme Commission number (EC number). The enzymes that can be prepared using the present method and apparatus are enzymes within all major EC classes: oxidoreductases (EC 1), transferases (EC 2), hydrolases (EC 3), lyases (EC 4), isomerases (EC 5) and ligases (EC 6). Some typical enzymes that can be produced using the bioreactor and methods described in the present document include alteplase, dornase alpha, reteplas, tenecteplase, alglucosidase alpha and idursulfase.

Other proteins and protein derivatives produced using the bioreactor and methods described in the present document include adrenocorticotropin hormones like adrenocorticotropin hormone and cosyntropin, corticotropin-releasing factors like coticorelin ocine triflate, cytokines like anakinra, consensus interferon, denileukin diftitox, interferon alpga, interferon beta, interferon gamma, interferon-1, interferon-2/aldesleukin, interferon-2 fusion protein, interleukin-11/oprelekin, gonadotropins like follitropin alpha, follitropin beta, lutropin alpha, monotropins and urofollitropin, gonadotropin-releasing hormones like abatelix, cetrorelix acetate, ganirelix acetate, gonadotropin-releasing hormone, goserelin acetate, histrelin acetate, leuprolide acetate, nafarelin acetate, triptorelin pamoate, growth hormones like pegvisomat and somatropin, hematopoietic growth factors like erythropoietin (epoetin alpha), filgrastim, pegfilgrastim and sargramostim, pancreatic hormones like amylin, glucagon and pramlintide acetate, parathyroid hormones like teriparatide, pituitary hormones like desmopressin acetate, oxytocin and vasopressin, placenteral hormones like vhoriogonadotropin alpha and human chorionic gonadotropin, thyroid hormones like calcitonin salmon, tumor necrosis factors like abatacept and etanercept, other and growth factors.

EXPERIMENTAL

The following examples are provided in order to demonstrate and further illustrate certain preferred embodiments and aspects of the present invention and are not to be construed as limiting the scope thereof.

Example 1

Production of Omalizumab

Omalizumab is an IgE/IgG kappa monoclonal antibody and is the active pharmaceutical ingredient in Xolair (Novartis) used for treatment of asthma.

The product is prepared according to the methods described in EP0682040 (Protein Design Labs) using a 100 liter disposable bioreactor according to the invention which comprises two compartments, for example a bioreactor as shown in FIG. 1 and described in the current text. The product is produced according to GMP, purified by chromatographic methods and other well-known processes described in the prior art. The final product is omalizumab with molecular formula C6450 H9916 N1714 O2023 S38 and CAS No. 242138-07-4. Omalizumab can, for example, be formulated as prefilled syringes or vial solutions comprising 75 mg or 150 mg omalizumab.

Example 2

Production of Palivizumab

Palivizumab is an IgG CD20 monoclonal antibody and is the active pharmaceutical ingredient in Arzerra (GSK) used for treatment of chronic lymphocytic leukaemia.

The product is prepared according to the methods described in EP0682040 (Protein Design Labs) using a 1000 liter stainless steel bioreactor according to the invention comprising two compartments, for example, as shown in FIG. 3 and described in the current text. The product is produced according to GMP, purified by chromatographic methods and other well-known processes described in the prior art. The final product is palivizumab with CAS No. 188039-54-5. Palivizumab can for example be formulated as a concentrate for infusion solutions comprising 20 mg palivizumab per ml.

Example 3

Production of a T4-Like Bacteriophage Infecting *Yersinia ruckeri*

Bacteriophage phiYrS-24-20-II (ACD Pharmaceuticals AS, Norway) is a T4-like bacteriophage infecting the fish pathogen *Yersinia ruckeri* YrS-24 (ACD Pharmaceuticals AS, Norway). The bacteriophage was grown to a titer of $2 \times 10^{10}$ pfu/mL in a 3 L disposable bioreactor according to the invention comprising three compartments as described in the current text and shown in FIG. 5. The disposable bioreactor was filled with 2.9 L sterile culture medium (17 g/L tryptone (supplied by Oxoid), 3 g/L yeast extract (supplied by Oxoid), 5 g/L NaCl (supplied by Merck), 2.5 g/L glucose (supplied by Merck), 10 mM $CaCl_2$ (supplied by Sigma-Aldrich)) and inoculated with 100 mL host bacterium, YrS-24, culture grown over night in a culture flask at 20° C. with 250 rpm shaking. The reaction was kept at 20° C. with 90 L/min sterile air sparging. Bacterial growth was monitored by optic density measurements at 600 nm (OD600). At an OD600 of 3.3, bacteriophages were added at a multiplicity of infection of approximately 10. The resulting infection was monitored by optic density measurements. After OD600 had first reached 7.6 and then dropped to 1.2, the culture was filtered at 0.22 μm and bacteriophages harvested from the filtrate.

Example 4

Production of Bacterial Vaccines and Vaccines Based on Antigens Expressed by Genetically Modified Bacteria Vaccines are produced according to the methods described in for example U.S. Pat. Nos. 5,616,328, 5,688,682, 6,022,728, 8,183,026, 6,790,950, 7,476,391, 4,981,685, 4,337,314, 8,440,207, 4,404,186, 6,248,570 or Appl. no. 20100183549 using a stainless steel multi-use or disposable, single use bioreactor according to the invention comprising two or three compartments as shown in FIGS. 1 and 3 and described in the current text. The vaccines are produced according to regulatory guidelines for pharmaceutical production and purified according to respective methods cited above.

Example 5

Production of Viral Vaccine From Recombinant Algae

Foot-and-mouth disease virus VP1 protein fused with cholera toxin B subunit is prepared as described by Sun et al. (Sun M., Qian K., Su N., Chang H. and Shen G. (2003) Foot-and-mouth disease virus VP1 protein fused with cholera toxin B subunit expressed in *Chlamydomonas reinhardtii* chloroplast. Biotechnol. Lett. 25(13): 1087-92) using a stainless steel or single use bioreactor comprising two or three compartments as shown in FIGS. 1 and 3 and described in the current text.

Other such vaccines as described and cited by Specht and Mayfield (Specht E. A. and Mayfield S. P (2014). Algae-based oral recombinant vaccines. Front. Microbiol. February 17, 5:60. doi: 10.3389), can similarly be produced using a stainless steel multi-use or disposable, single use bioreactor according to the invention comprising two or three compartments as shown in FIGS. 1 and 5, and described in the current text.

Example 6

Manufacture of a 3 Liter Disposable Bioreactor With Two Compartments

Two sheets of plastic (laminate of nylon (PA) and polyethylene (PE), 145 my) were welded together according to the welds shown as hatched areas in FIG. 7, so as to form two compartments and connections between the two compartments. Dimensions are shown in FIG. 7. To form connections for liquid input and output, a monitor loop and gas input and output, two pieces of HDPE300 having holes and hose fittings according to connections shown in FIG. 1 were welded in between the sheets at the side and on top of the reactor, as illustrated in FIG. 1.

Gas input was connected to a ceramic gas sparger inside the fermentation chamber of the bioreactor as shown in FIG. 1. A sterile filter (supplied by Millipore) was connected to the gas input connection outside the reactor. A 50 cm silicone hose of diameter 6 mm (supplied by VWR) was placed between the sterile filter and the bioreactor gas input in order to elevate the filter above liquid level and thus avoid possible backflow of liquid into filter material. Hose fittings for liquid input and output, and monitor loop, were connected to 6 mm silicone hoses of suitable length and closed off with hose clamps. The gas outlet hose fitting was connected to a 24 mm hose of length 20 cm which had been fitted with a sterile filter at the opposite end. A hose clamp was placed between the reactor and the gas outlet filter in order to facilitate manual control of reactor internal gas pressure.

Example 7

Production of Insulin

Insulin glulisine is a rapid-acting human insulin analogue that differs from human insulin in that the amino acid asparagine at position B3 is replaced by lysine and the lysine in position B29 is replaced by glutamic acid.

The product is prepared according to the methods described in U.S. Pat. No. 6,221,633 (Aventis Pharma) using a 500 liter stainless steel multi-use bioreactor according to the invention comprising two compartments as shown in FIGS. 1, 3 and 8 and described in the current text. The product is produced according to GMP, purified by chromatographic methods and other well-known processes described in the prior art. The final product is insulin glulisine with CAS No. 207748-29-6. Insulin glulisine can for example be formulated as injection solution comprising 100 IU per ml. Other components in the final solution can typically be metacresol, sodium chloride, trometamol, polysorbate 20, hydrochloric acid, sodium hydroxide and water for injections.

Various aspects of the invention may be defined by the following additional clauses which should not be taken is limiting on the invention:

Clause 1. A bioreactor, comprising: at least one fermentation compartment and at least one foam compartment where foam is transported back to the fermentation mixture in the form of liquid, wherein said fermentation and foam compartments are separated by a wall that is absent or permeable for foam in the upper part of the reactor and is absent or permeable for liquid in a lower part of the reactor.

Clause 2. The bioreactor of clause 1, wherein said bioreactor comprises at least two fermentation compartments.

Clause 3. The bioreactor of clause 1, wherein said bioreactor comprises at least two foam components.

Clause 4. The bioreactor of clause 1, wherein said bioreactor further comprises a gas sparger.

Clause 5. The bioreactor of clause 4, wherein said gas sparger comprises a gas inlet and/or a propeller.

Clause 6. The bioreactor of clause 5, wherein said propeller is a magnetic propeller.

Clause 7. The bioreactor of clause 1, wherein said bioreactor further comprises a gas outlet filter and a pressure control.

Clause 8. The bioreactor of clause 7, wherein said gas outlet and said pressure control are on the same assembly.

Clause 9. The bioreactor of clause 7, wherein said gas outlet and said pressure control are in physically different locations of said bioreactor.

Clause 10. The bioreactor of clause 1, wherein said bioreactor comprises a foam transfer component configured to transfer foam from said fermentation compartment to said foam compartment.

Clause 11. The bioreactor of clause 1, wherein said bioreactor further comprises a culture transfer component configured to recycle cultures to said fermentation compartment.

Clause 12. The bioreactor of clause 1, wherein said bioreactor further comprises at least one component selected from a filling inlet, a filling outlet, and a monitor loop.

Clause 13. The bioreactor of clause 1, wherein said bioreactor is disposable.

Clause 14. The bioreactor of clause 1, wherein said foam transport component transports foam based on gravity.

Clause 15. The bioreactor of clause 1, wherein said bioreactor is a gas-lift reactor.

Clause 16. The bioreactor of clause 1, wherein said bioreactor further comprises a waste compartment.

Clause 17. The use of the bioreactor of any one of clauses 1 to 16 in the fermentation of a living organism or active component thereof.

Clause 18. The use of clause 17, wherein said organism is selected from a bacterium, a virus, an animal cell, an insect cell, a plant cell, a fungus, an algal cell, a protist cell, an archaea cell, and active components thereof.

Clause 19. The use of clause 18, wherein said animal cell is a human cell.

Clause 20. The use of clause 18, wherein said virus is a bacteriophage.

Clause 21. The use of clause 17, wherein said fermentation is anaerobic or aerobic.

Clause 22. The use of clause 17, wherein said fermentation produces a drug, active pharmaceutical agent, or drug precursor.

Clause 23. The use of clause 22, wherein said drug, active pharmaceutical agent, or drug precursor is a protein, a protein derivative, or a small molecule.

Clause 24. The use of clause 17, wherein said fermentation produces a living non-human organism.

Clause 25. The use of clause 24, wherein said living non-human organism is for use in a pharmaceutical product.

Clause 26. The use of clause 23, wherein said protein is an antibody.

Clause 27. The use of clause 22 or 25, wherein said drug, active pharmaceutical agent, living non-human organism or drug precursor is for use in the treatment of cancer, infections, or immunological disease.

Clause 28. The use of clause 17, wherein the loss of fermentation product is reduced by at least one half relative to the loss in a one-compartment reactor.

Clause 29. A method, comprising: contacting the bioreactor of any one of clauses 1 to 16 with a living organism or active component thereof under conditions such that a fermentation reaction occurs.

Clause 30. The method of clause 29, wherein said organism is selected from bacterium, a virus, an animal cell, an insect cell, a plant cell, a fungus, an algal cell, a protist cell, an archaea cell, and active components thereof.

Clause 31. The method of clause 30, wherein said animal cell is a human cell.

Clause 32. The method of clause 30, wherein said virus is a bacteriophage.

Clause 33. The method of clause 29, wherein said fermentation is anaerobic or aerobic.

Clause 34. The method of clause 29, wherein said fermentation produces a drug, active pharmaceutical agent, or drug precursor.

Clause 35. The method of clause 34, wherein said drug, active pharmaceutical agent, or drug precursor is a protein, a protein derivative, or a small molecule.

Clause 36. The method of clause 29, wherein said fermentation produces a living non-human organism.

Clause 37. The method of clause 36, wherein said living non-human organism is for use in a pharmaceutical product.

Clause 38. The method of clause 35, wherein said protein is an antibody.

Clause 39. The method of clause 34 or 37, wherein said drug, active pharmaceutical agent, living non-human organism or drug precursor is for use in the treatment of cancer, infections, or immunological disease.

Clause 40. The method of clause 29, wherein the loss of fermentation product is reduced by at least one half relative to the loss in a one-compartment reactor.

The invention claimed is:

1. A single use, disposable bioreactor formed from plastic comprising:
   a reaction chamber having a fermentation zone at is lowest part and a foam settling zone at its upper part, with the foam settling zone being formed as a laterally enlarged section of the reaction chamber and being situated above a level of liquid present in the reaction chamber, when the single use, disposable, plastic bioreactor is in use, wherein the reaction chamber is arranged such that the foam settling zone is spaced from the fermentation zone so as to reduce the effect of activity in the fermentation zone on a foam in the settling zone, and wherein a barrier is disposed so as to partially separate the fermentation zone from the foam settling zone, wherein the barrier forms a large aperture for passage of foam from the fermentation zone to the foam settling zone and a small aperture for passage of settled as liquid from the foam settling zone to the fermentation zone.

2. The bioreactor as claimed in claim 1, wherein the foam settling zone is positioned to one side of the fermentation zone.

3. The bioreactor as claimed in claim 1, wherein the foam settling zone has a bottom wall that slopes downwardly towards the fermentation zone so that settled foam can flow as liquid back to the fermentation zone under gravity.

4. The bioreactor as claimed in claim 1, wherein the small aperture connects to a lower part of the fermentation zone.

5. The bioreactor as claimed in claim 4, wherein the small aperture is arranged to drain liquid onto a wall of the reaction chamber.

6. The bioreactor as claimed in claim 1, wherein a separator separates the fermentation zone from the foam settling zone and wherein the separator comprises a large aperture for passage of foam from the fermentation zone to the foam settling zone and a small aperture for passage of settled foam as liquid from the foam settling zone to the fermentation zone.

7. The bioreactor as claimed in claim 1, wherein a gas outlet is provided in an upper region of the foam settling zone.

8. The bioreactor as claimed in claim 1, further comprising a waste chamber fluidly connected to an upper portion of the foam settling zone and further comprising a gas outlet located in the waste chamber.

9. The bioreactor as claimed in claim 8, wherein the waste chamber is located underneath the foam settling zone and adjacent the fermentation zone.

10. The bioreactor as claimed in claim 1, formed from two flexible sheets overlapped with each other and welded together to form the reaction chamber and any additional internal structure.

11. The bioreactor as claimed in claim 1, comprising a mixing device at a lower portion of the fermentation zone.

12. The bioreactor as claimed in claim 1, formed from one or more cylindrical tubes.

13. A bioreactor comprising:
   a reaction chamber having a fermentation zone and a foam settling zone, wherein the reaction chamber is arranged such that the foam settling zone is spaced from or physically separated from the fermentation zone so as to reduce the effect of activity in the fermentation zone on foam in the settling zone; and
   a waste chamber fluidly connected to an upper portion of the foam settling zone and further comprising a gas outlet located in the waste chamber.

14. The bioreactor as claimed in claim 13, wherein the waste chamber is located underneath the foam settling zone and adjacent the fermentation zone.

* * * * *